(12) United States Patent
Amako et al.

(10) Patent No.: US 8,710,427 B2
(45) Date of Patent: *Apr. 29, 2014

(54) SENSOR CHIP, SENSOR CARTRIDGE, AND ANALYSIS APPARATUS

(75) Inventors: Jun Amako, Matsumoto (JP); Kohei Yamada, Minowa (JP)

(73) Assignee: Seiko Epson Corporation (JP)

( * ) Notice: Subject to any disclaimer, the term of this patent is extended or adjusted under 35 U.S.C. 154(b) by 479 days.

This patent is subject to a terminal disclaimer.

(21) Appl. No.: 12/949,142

(22) Filed: Nov. 18, 2010

(65) Prior Publication Data

US 2011/0114859 A1    May 19, 2011

(30) Foreign Application Priority Data

Nov. 19, 2009  (JP) ................... 2009-263706
Dec. 11, 2009  (JP) ................... 2009-281480
Aug. 30, 2010  (JP) ................... 2010-192838
Aug. 30, 2010  (JP) ................... 2010-192839

(51) Int. Cl.
    *G01N 21/27*    (2006.01)
    *G01D 5/36*     (2006.01)
    *G02B 5/18*     (2006.01)

(52) U.S. Cl.
    USPC .............. 250/237 G; 250/576; 359/569

(58) Field of Classification Search
    USPC ........... 250/237 G, 237 R, 573, 576; 349/96; 359/486.01, 486.02, 486.03, 569
    See application file for complete search history.

(56) References Cited

U.S. PATENT DOCUMENTS

| 5,477,351 | A  | * | 12/1995 | Takahara et al. ............ 349/5 |
| 5,986,762 | A  |   | 11/1999 | Challener |
| 6,810,057 | B1 | * | 10/2004 | Itoh et al. ................ 372/50.1 |
| 7,388,661 | B2 |   | 6/2008  | Li et al. |
| 7,722,194 | B2 |   | 5/2010  | Amako et al. |
| 7,755,718 | B2 |   | 7/2010  | Amako et al. |
| 7,972,017 | B2 | * | 7/2011  | Amako et al. ............... 353/98 |

(Continued)

FOREIGN PATENT DOCUMENTS

| JP | 10-274631   | 10/1998 |
| JP | 2000-356587 | 12/2000 |

(Continued)

OTHER PUBLICATIONS

Li, Lifeng et al., "Convergence of the Coupled-Wave Method for Metallic Lamellar Diffraction Gratings", Optical Society of America, Optical Sciences Center, University of Arizona, vol. 10, No. 6, Jun. 1993, pp. 1184-1189.

(Continued)

*Primary Examiner* — John Lee
(74) *Attorney, Agent, or Firm* — Harness, Dickey & Pierce, P.L.C.

(57) ABSTRACT

A sensor chip includes: a substrate that has a planar portion; and a diffraction grating, on which a target substance is placed, that includes a plurality of first protrusions periodically arranged in a period equal to or greater than 100 nm and equal to or less than 1000 nm in a first direction that is parallel to the planar portion, a plurality of base portions that is located between two of the first protrusions adjacent to each other and configures a base of the substrate, and a plurality of second protrusions that is formed on upper faces of the plurality of the first protrusions, has a surface formed from a metal, and is formed on the planar portion.

20 Claims, 17 Drawing Sheets

(56) References Cited

U.S. PATENT DOCUMENTS

| | | | |
|---|---|---|---|
| 8,208,191 B2* | 6/2012 | Gan et al. | 359/288 |
| 8,221,963 B2* | 7/2012 | Amako et al. | 430/321 |
| 8,323,564 B2* | 12/2012 | Padmanabhan et al. | 422/63 |
| 8,415,611 B2* | 4/2013 | Amako et al. | 250/237 G |
| 2004/0155309 A1* | 8/2004 | Sorin et al. | 257/433 |
| 2008/0218761 A1 | 9/2008 | Nishikawa et al. | |
| 2008/0304004 A1 | 12/2008 | Amako et al. | |
| 2009/0170038 A1 | 7/2009 | Amako et al. | |
| 2010/0020400 A1 | 1/2010 | Amako | |
| 2010/0188747 A1 | 7/2010 | Amako et al. | |
| 2010/0238555 A1 | 9/2010 | Amako et al. | |
| 2011/0114859 A1* | 5/2011 | Amako et al. | 250/576 |
| 2011/0116088 A1* | 5/2011 | Amako et al. | 356/300 |
| 2012/0091372 A1* | 4/2012 | Molnar et al. | 250/550 |

FOREIGN PATENT DOCUMENTS

| | | |
|---|---|---|
| JP | 2008-203553 | 9/2008 |
| JP | 2009-015302 | 1/2009 |
| JP | 2009-015305 | 1/2009 |
| JP | 2009-064005 | 3/2009 |
| JP | 2009-134287 | 6/2009 |
| JP | 2009-175707 | 8/2009 |
| JP | 2009-222507 A | 10/2009 |
| JP | 2009-250951 A | 10/2009 |

OTHER PUBLICATIONS

Extended European Search Report for Application No. EP 10 19 1511 mailed Sep. 3, 2012 (7 pages).

Kubo, Atsushi et al. "Femtosecond Microscopy of Localized and Propagating Surface Plasmons in Silver Gratings", Journal of Physics B, Atomic, Molecular and Optical Physics, Institute of Physics Publishing, Bristol, GB, vol. 40, No. 11, Jun. 14, 2007, Sections 1 and 3.1 pp. S259-S272.

Barnes, William L. et al., "Surface Plasmon Subwavelength Optics", Nature: International Weekly Journal of Science, Nature Publishing Group, United Kingdom, vol. 424, Aug. 14, 2003, pp. 824-830.

Extended European Search Report for Application No. 10 19 1512 mailed Sep. 3, 2012 (9 pages).

Heinz, Andreas Nicol, "Grating Coupled Surface Plasmon Enhanced Fluorescence Spectroscopy", Johannes Gutenberg—Universität Mainz, Germany, Nov. 11, 2005, pp. 1-169.

Andreas Heinz Nicol, "Grating Coupled Surface Plasmon Enhanced Fluorescence Spectroscopy", Sep. 2005, (URL: http://www2.mpip-mainz.mpg.de/groups/knoll/publication/theses/2005/nicol_2005), pp. 47-63.

* cited by examiner

SENSOR CHIP, SENSOR CARTRIDGE, AND ANALYSIS APPARATUS

CROSS REFERENCES TO RELATED APPLICATIONS

The present application claims priority to Japanese Patent Application Nos. 2009-263706 filed Nov. 19, 2009, and 2010-192839 filed Aug. 30, 2010 the entire contents of which are incorporated herein by reference.

BACKGROUND

1. Technical Field

The present invention relates to a sensor chip, a sensor cartridge, and an analysis apparatus.

2. Related Art

Recently, demand for sensors used for medical diagnoses, inspection of food, and the like has been increasing, and thus development of sensor technology that implements a sensor that is miniaturized and can sense at a high speed is in demand. In order to respond to such demand, various types of sensors using electrochemical techniques and the like have been reviewed. Among these, from the viewpoint of easy integration, low cost, and low sensitivity to the measurement environment, sensors using surface plasmon resonance (SPR) have drawn attention.

Here, the surface plasmon is an oscillation mode of an electron wave that is coupled with light depending on the boundary condition specific to the surface. As a method of exciting the surface plasmon, there is a method in which a diffraction grating is imprinted on a metal surface and light and plasmon are coupled together or a method in which an evanescent wave is used. For example, as a configuration of a sensor that uses SPR, a configuration in which a total reflection-type prism and a metal film brought into contact with a target substance that is formed on the surface of the prism are included is known. According to such a configuration, it is detected whether or not a target substance is adsorbed including whether or not an antigen is adsorbed in an antigen-antibody reaction and the like.

However, while propagation-type surface plasmon is present on the metal surface, localized-type surface plasmon exists in a metal fine particle. It is known that, when the localized-type surface plasmon, that is, the surface plasmon that exists locally on the microstructure of the surface is excited, a markedly enhanced electric field is generated.

Thus, in order to improve the sensitivity of the sensor, a sensor that uses a localized surface plasmon resonance (LSPR) using metal fine particles or metal nanostructures is proposed. For example, in JP-A-2000-356587, by irradiating light onto a transparent substrate having a surface to which metal fine particles are fixed in a film shape and measuring the absorbance of light being transmitted through the metal fine particles, a change in the medium near the metal fine particles is detected, whereby adsorption or deposition of a target substance is detected.

However, according to JP-A-2000-356587, it is difficult to produce metal fine particles that have a uniform size (dimension or shape) and to regularly arrange the metal fine particles. When the size or the arrangement of the metal fine particles cannot be controlled, there are variations in absorption due to resonance or a resonant wavelength. Accordingly, the width of the absorbance spectrum becomes broad, and the peak intensity decreases. Accordingly, a change in the signal detecting the change in the medium near the metal fine particles is low, and there are limitations on improving the sensitivity of the sensor. Therefore, the sensitivity of the sensor is insufficient for use in specifying a substance from the absorbance spectrum or the like.

SUMMARY

An advantage of some aspects of the invention is that it provides a sensor chip, a sensor cartridge, and an analysis apparatus capable of specifying a target substance from a Raman spectroscopic spectrum by improving the sensitivity of a sensor.

The aspects of the invention employ the following configurations.

According to a first aspect of the invention, there is provided a sensor chip including: a substrate that has a planar portion; and a diffraction grating on the planar portion and having a metal surface, the diffraction having a target substance thereon and including: a plurality of first protrusions periodically arranged in a period equal to or greater than 100 nm and equal to or less than 1000 nm in a first direction that is parallel to the planar portion, a plurality of base portions that is located between two adjacent first protrusions and configures a base of the substrate, and a plurality of second protrusions on upper faces of the plurality of the first protrusions.

According to the first aspect of the invention, a proximal electric field that is enhanced through surface plasmon resonance by the first protrusions is excited toward the surface having the same shape, and surface enhanced Raman scattering (SERS) having a high degree of enhancement can be further exhibited by a metallic microstructure due to the second protrusions. More specifically, when light is incident to a face on which a plurality of the first protrusions and a plurality of the second protrusions are formed, a surface-specific oscillation mode (surface plasmon) according to the plurality of the first protrusions is formed. Then, free electrons are in the state of resonant oscillation in accordance with the oscillation of light, and accordingly, the oscillation of an electromagnetic wave is excited in accordance with the oscillation of the free electrons. Since the oscillation of the free electrons is influenced by the oscillation of this electromagnetic wave, a system acquired by coupling the oscillations of both parties, that is, a so-called surface plasmon polariton (SPP) is formed. Accordingly, localized surface plasmon resonance (LSPR) is excited near the plurality of the second protrusions. In this structure, since a distance between two of the second protrusions adjacent to each other is short, an extremely strong enhanced electric field is generated near the contact points thereof. Then, when one to several target substances are adsorbed to the contact points, the SERS occurs from the contact points. Accordingly, a sharp SERS spectrum that is specific to the target substance can be acquired. Therefore, a sensor chip capable of specifying a target substance from an SERS spectrum by improving the sensitivity of the sensor can be provided. By appropriately changing the period and the height of the first protrusion and the height of the second protrusion, the position of the resonant peak can be adjusted to an arbitrary wavelength. Accordingly, it is possible to appropriately select the wavelength of light that is emitted for specifying a target substance, whereby the width of the measurement range increases.

In the above-described sensor chip, it is preferable that the plurality of first protrusions is periodically arranged in a second direction that intersects the first direction and is parallel to the planar portion. In such a case, sensing can be performed under a condition of plasmon resonance that is broader than that of a case where the first protrusions are formed to have periodicity only in the direction (the first direction) parallel to the planar portion of the substrate. Accordingly, a sensor chip capable of specifying a target substance from an SERS spectrum by improving the sensitivity of the sensor can be provided. Furthermore, in addition to the period of the first protrusions in the first direction, the period in the second direction can be appropriately changed. Accordingly, it is possible to appropriately select the wavelength of light that is emitted for specifying a target substance, whereby the width of the measurement range increases.

In the above-described sensor chip, it is preferable that the plurality of second protrusions is periodically arranged in a third direction that is parallel to the planar portion. In such a case, the period of the second protrusions can be appropriately changed. Accordingly, it is possible to appropriately select the wavelength of light that is emitted for specifying a target substance, whereby the width of the measurement range increases.

In the above-described sensor chip, it is preferable that the plurality of second protrusions is periodically arranged in a fourth direction that intersects the third direction and is parallel to the planar portion. In such a case, sensing can be performed under a condition of plasmon resonance that is broader than that of a case where the second protrusions are formed only in the direction (the third direction) parallel to the planar portion of the substrate. Accordingly, a sensor chip capable of specifying a target substance from an SERS spectrum by improving the sensitivity of the sensor can be provided. Furthermore, in addition to the period of the second protrusions in the third direction, the period in the fourth direction can be appropriately changed. Accordingly, it is possible to appropriately select the wavelength of light that is emitted for specifying a target substance, whereby the width of the measurement range increases.

In the above-described sensor chip, it is preferable that the plurality of second protrusions is formed from fine particles. In such a case, a sensor chip capable of specifying a target substance from an SERS spectrum by improving the sensitivity of the sensor can be provided.

In the above-described sensor chip, it is preferable that, when a width of the first protrusion in the first direction is denoted by W1, and a distance between two adjacent first protrusions in the first direction is denoted by W2, relationship of "W1>W2" is satisfied. In such a case, the spatial filling rate of the first protrusions in which the LSPR is excited increases. Therefore, sensing can be performed under a condition of plasmon resonance that is broader than that of a case where the relationship of "W1<W2" is satisfied. In addition, the energy of light emitted for specifying a target substance can be effectively used.

In the above-described sensor chip, it is preferable that a ratio of the width W1 of the first protrusion in the first direction to the distance W2 between the two adjacent first protrusions in the first direction satisfies relationship of "W1:W2=9:1". In such a case, sensing can be performed under a condition of broad plasmon resonance. In addition, the energy of light emitted for specifying a target substance can be effectively used.

In the above-described sensor chip, it is preferable that the metal surface of the diffraction grating is one of gold and silver. In such a case, since gold or silver has a characteristic for exhibiting the SPP, the LSPR, and the SERS, the SPP, the LSPR, and the SERS can be easily exhibited, whereby a target substance can be detected with high sensitivity.

According to a second aspect of the invention, there is provided a sensor cartridge including: the above-described sensor chip; a transport unit that transports the target substance to a surface of the sensor chip; a placement unit in which the sensor chip is placed; a casing that houses the sensor chip, the transport unit, and the placement unit; and an irradiation window that is disposed at a position facing the surface of the sensor chip on the casing.

According to the second aspect of the invention, since the above-described sensor chip is included, a target molecule can be detected by performing selective spectroscopy for the Raman scattering light. Therefore, a sensor cartridge capable of specifying a target substance from the SERS spectrum by improving the sensitivity of the sensor can be provided.

According to a third aspect of the invention, there is provided an analysis apparatus including: the above-described sensor chip; a light source that emits light to the sensor chip; and a photo detector that detects light scattered by the sensor chip.

According to the third aspect of the invention, since the above-described sensor chip is included, a target molecule can be detected by performing selective spectroscopy for the Raman scattering light. Therefore, an analysis apparatus capable of specifying a target substance from an SERS spectrum by improving the sensitivity of the sensor can be provided.

According to a fourth aspect of the invention, there is provided a sensor chip including: a substrate that has a planar portion; and a diffraction grating having a composite pattern in the planar portion and a metal surface, the diffraction grating having a target substance thereon and superimposedly including: a first protrusion pattern in which a plurality of first protrusions is periodically arranged in a period equal to or greater than 100 nm and equal to or less than 1000 nm and a second protrusion pattern in which a plurality of second protrusions is periodically arranged in the plurality of first protrusions in a period shorter than that of the first protrusion pattern.

According to the fourth aspect of the invention, a proximal electric field that is enhanced through surface plasmon resonance by the first protrusion is excited toward the surface having the same shape, and surface enhanced Raman scattering (SERS) having a high degree of enhancement can be further exhibited by a metallic microstructure due to the second protrusion. More specifically, when light is incident to a face on which the first protrusion pattern and the second protrusion pattern are formed, a surface-specific oscillation mode (surface plasmon) according to the first protrusion pattern is formed. Then, free electrons are in the state of resonant oscillation in accordance with the oscillation of light, and accordingly, the oscillation of an electromagnetic wave is excited in accordance with the oscillation of the free electrons. Since the oscillation of the free electrons is influenced by the oscillation of this electromagnetic wave, a system acquired by coupling the oscillations of both the parties, that is, a so-called surface plasmon polariton (SPP) is formed. Accordingly, localized surface plasmon resonance (LSPR) is excited near the second protrusion pattern. In this structure, since a distance between two of the second protrusions adjacent to each other is short, an extremely strong enhanced electric field is generated near the contact points thereof. Then, when one to several target substances are adsorbed to the contact points, the SERS occurs from the contact points. Accordingly, a sharp SERS spectrum that is specific to the target substance can be acquired. Therefore, a sensor chip capable of specifying a target substance from an SERS spectrum by improving the sensitivity of the sensor can be provided. By appropriately changing the period and the height of the first protrusion and the height of the second protrusion, the position of the resonant peak can be adjusted to an arbitrary wavelength. Accordingly, it is possible to appropriately select the wavelength of light that is emitted for specifying a target substance, whereby the width of the measurement range increases.

In the above-described sensor chip, it is preferable that the plurality of first protrusions is periodically arranged in a first direction that is parallel to the planar portion and is periodically arranged in a second direction that intersects the first direction and is parallel to the planar portion. In such a case, sensing can be performed under a condition of plasmon resonance that is broader than that of a case where the first protrusions are formed to have periodicity only in the direction (the first direction) parallel to the planar portion of the substrate. Accordingly, a sensor chip capable of specifying a target substance from an SERS spectrum by improving the sensitivity of the sensor can be provided. Furthermore, in addition to the period of the first protrusions in the first direction, the period in the second direction can be appropriately changed. Accordingly, it is possible to appropriately select the wavelength of light that is emitted for specifying a target substance, whereby the width of the measurement range increases.

In the above-described sensor chip, it is preferable that the plurality of second protrusions is periodically arranged in a third direction that is parallel to the planar portion. In such a case, the period of the second protrusions can be appropriately changed. Accordingly, it is possible to appropriately select the wavelength of light that is emitted for specifying a target substance, whereby the width of the measurement range increases.

In the above-described sensor chip, it is preferable that the plurality of second protrusions is periodically arranged in a fourth direction that intersects the third direction and is parallel to the planar portion. In such a case, sensing can be performed under a condition of plasmon resonance that is broader than that of a case where the second protrusions are formed only in the direction (the third direction) parallel to the planar portion of the substrate. Accordingly, a sensor chip capable of specifying a target substance from an SERS spectrum by improving the sensitivity of the sensor can be provided. Furthermore, in addition to the period of the second protrusions in the third direction, the period in the fourth direction can be appropriately changed. Accordingly, it is possible to appropriately select the wavelength of light that is emitted for specifying a target substance, whereby the width of the measurement range of the measurement range increases.

In the above-described sensor chip, it is preferable that the plurality of second protrusions is formed from fine particles. In such a case, a sensor chip capable of specifying a target substance from an SERS spectrum by improving the sensitivity of the sensor can be provided.

In the above-described sensor chip, it is preferable that, when a width of the first protrusion in the first direction is denoted by W1, and a distance between two adjacent first protrusions in the first direction is denoted by W2, relationship of "W1>W2" is satisfied. In such a case, the spatial filling rate of the first protrusions in which the LSPR is excited increases. Therefore, sensing can be performed under a condition of plasmon resonance that is broader than that of a case where the relationship of "W1<W2" is satisfied. In addition, the energy of light emitted for specifying a target substance can be effectively used.

In the above-described sensor chip, it is preferable that a ratio of the width W1 of the first protrusion in the first direction to the distance W2 between the two adjacent first protrusions in the first direction satisfies relationship of "W1: W2=9:1". In such a case, sensing can be performed under a condition of broad plasmon resonance. In addition, the energy of light emitted for specifying a target substance can be effectively used.

In the above-described sensor chip, it is preferable that the metal that composes the surface of the diffraction grating is gold or silver. In such a case, since gold or silver has a characteristic for exhibiting the SPP, the LSPR, and the SERS, the SPP, the LSPR, and the SERS can be easily exhibited, whereby a target substance can be detected with high sensitivity.

According to a fifth aspect of the invention, there is provided a sensor cartridge including: the above-described sensor chip; a transport unit that transports the target substance to a surface of the sensor chip; a placement unit in which the sensor chip is placed; a casing that houses the sensor chip, the transport unit, and the placement unit; and an irradiation window that is disposed at a position facing the surface of the sensor chip on the casing.

According to the fifth aspect of the invention, since the above-described sensor chip is included, a target molecule can be detected by performing selective spectroscopy for the Raman scattering light. Therefore, a sensor cartridge capable of specifying a target substance from the SERS spectrum by improving the sensitivity of the sensor can be provided.

According to a sixth aspect of the invention, there is provided an analysis apparatus including: the above-described sensor chip; a light source that emits light onto the sensor chip; and a photo detector that detects light scattered by the sensor chip.

According to the sixth aspect of the invention, since the above-described sensor chip is included, a target molecule can be detected by performing selective spectroscopy for the Raman scattering light. Therefore, an analysis apparatus capable of specifying a target substance from an SERS spectrum by improving the sensitivity of the sensor can be provided.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1A:
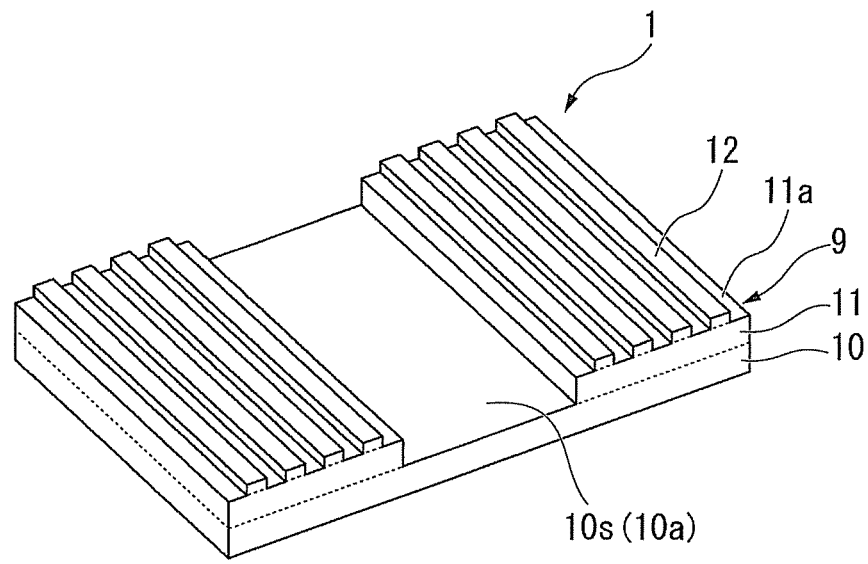
FIGS. 1A and 1B are schematic diagrams representing a schematic configuration of a sensor chip according to an embodiment of the invention.

Hereinafter, an embodiment of the invention will be described with reference to the accompanying drawings. Such an embodiment represents one aspect of an embodiment of the invention and is not for the purpose of limiting the invention. Thus, various changes can be arbitrarily made therein within the technical scope of the invention. In the drawings described below, for easy understanding of each configuration, the scales, the numbers, and the like of structures are different from those of the actual structures.

Figure 1B:
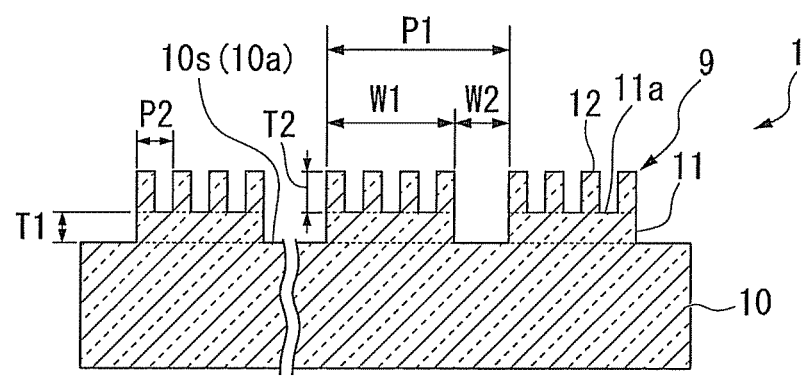

FIGS. 1A and 1B are schematic diagrams representing a schematic configuration of a sensor chip according to an embodiment of the invention. FIG. 1A is a perspective view of the sensor chip showing a schematic configuration thereof. FIG. 1B is a schematic cross-sectional view representing the configuration of the sensor chip. In FIG. 1B, reference sign P1 is a period of the first protrusion (the first convex shape), reference sign P2 is a period of the second protrusion (the second convex shape), reference sign W1 represents the width of the first protrusion, reference sign W2 is a distance between two of the first protrusions that are adjacent to each other, reference sign T1 is the height of the first protrusion (the depth of the groove), and a reference sign T2 is the height of the second protrusion (the depth of the groove).

Figure 19:
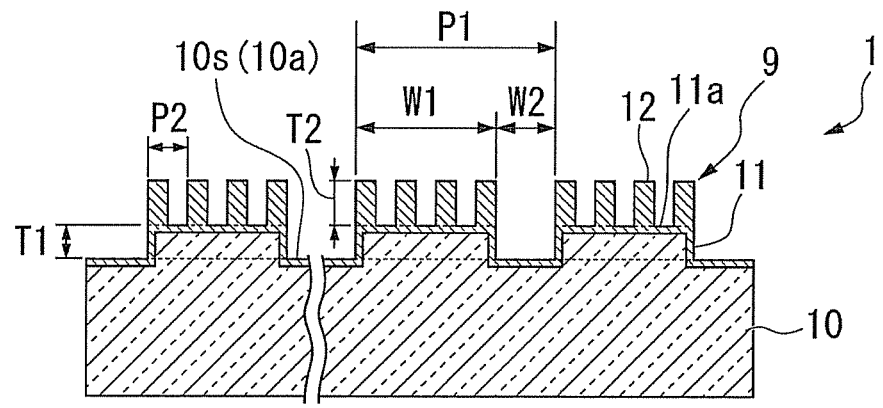
FIG. 19 is a schematic diagram showing a schematic configuration of a sensor chip according to an embodiment of the invention.
Figure 20:
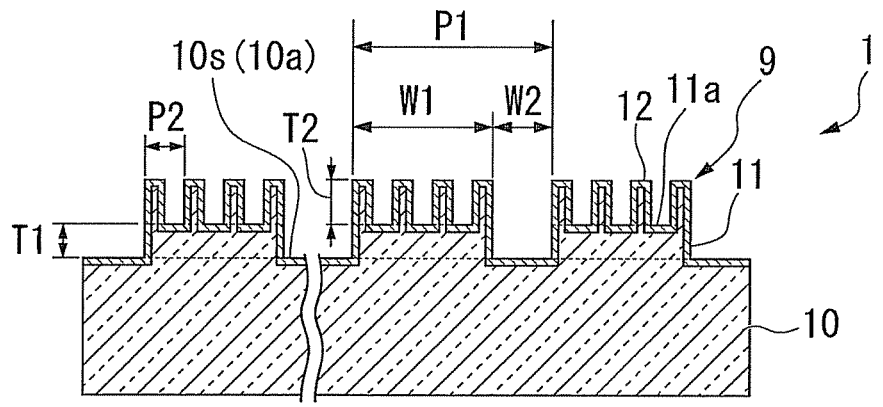
FIG. 20 is a schematic diagram showing a schematic configuration of a sensor chip according to an embodiment of the invention.

FIGS. 19 and 20 are schematic diagrams showing the schematic configurations of sensor chips according to an embodiment of the invention, which correspond to FIG. 1B. In FIGS. 19 and 20, reference sign P1 is a period of the first protrusion (the first convex shape), reference sign P2 is a period of the second protrusion (the second convex shape), reference sign W1 represents the width of the first protrusion, reference sign W2 is a distance between two of the first protrusions that are adjacent to each other, reference sign T1 is the height of the first protrusion (the depth of the groove), and reference sign T2 is the height of the second protrusion (the depth of the groove).

The sensor chip 1 is used for placing a target substance in a diffraction grating 9 that is formed in a substrate 10 containing metal and detecting the target substance by using localized surface Plasmon resonance (LSPR) and surface enhanced Raman scattering (SERS).

The diffraction grating 9 includes: a plurality of the first protrusions 11 that is arranged in a period P1 equal to or greater than 100 nm and equal to or less than 1000 nm in the first direction that is parallel to a planar portion of the substrate 10; a plurality of base portions 10a that is positioned between two of the first protrusions 11 adjacent to each other and configures the base of the substrate 10; and a plurality of the second protrusions 12 that is formed on an upper face 11a of each of the plurality of the first protrusions 11. The diffraction grating 9 has a surface formed from metal and is formed on a planar portion 10s of the substrate 10.

In other words, the diffraction grating 9 has a composite pattern acquired by superimposing the first protrusion pattern in which the first protrusions (the first convex shapes) 11 arranged in a period P1 equal to or greater than 100 nm and equal to or less than 1000 nm in a direction perpendicular to the planar portion 10s of the substrate 10 and the second protrusion pattern in which the second protrusions (the second convex shapes) 12 are arranged in a period P2 shorter than that of the first protrusion pattern in each of the plurality of the first protrusions 11 and has a surface formed from metal. And the protrusions could also have a rounded/convex shape rather than the rectangular shape shown in the drawings.

The "diffraction grating" described here represents a structure in which a plurality of protrusion patterns (a plurality of protrusions) is periodically arranged.

In addition, the "planar portion" described here represents the upper face portion of the substrate. In other words, the "planar portion" represents one surface portion of the substrate on which a target substance is placed. The composite pattern that is formed by superimposing the first protrusion pattern and the second protrusion pattern is formed on at least the upper face portion of the substrate. The shape of the other surface portion, that is, the lower face portion of the substrate is not particularly limited. However, in consideration of the processing process or the like performed for the planar portion (the upper face portion) of the substrate, it is preferable that the lower face portion of the substrate is parallel to the base portion of the planar portion and is a flat face.

As an example of the configuration of the diffraction grating 9, as shown in FIG. 1B, there is a structure in which the substrate 10, the first protrusion 11, and the second protrusion 12 are all formed from metal. In addition, as shown in FIG. 19, there is a structure in which the substrate 10 and the first protrusion 11 are formed by an insulating member formed from glass, resin, or the like, all the exposed portions of the insulating member are covered with a metal film, and the second protrusion 12 formed from metal is formed on the metal film. In addition, as shown in FIG. 20, there is a structure in which all the substrate 10, the first protrusion 11, and the second protrusion 12 are formed by an insulating member, and all the exposed portions of the insulating member are covered with a metal film. In other words, the diffraction grating 9 has a configuration in which the base portion 10a of the substrate 10 and at least the surfaces of the first protrusion 11 and the second protrusion 12 are formed from metal.

The substrate 10, for example, has a structure in which a metal film having a thickness of 150 nm or more is formed on a glass substrate. This metal film becomes the first protrusion 11 and the second protrusion 12 through a manufacturing process to be described later. In this embodiment, the substrate 10 in which the metal film is formed on the glass substrate is used. However, the substrate 10 is not limited thereto. For example, a substrate in which a metal film is formed on a quartz substrate or sapphire substrate may be used as the substrate 10. In addition, a flat plate formed from metal may be used as the substrate.

The first protrusions 11 are formed on the planar portion 10s of the substrate 10 so as to have a predetermined height T1. These first protrusions 11 are arranged in a period P1 that is shorter than the light wavelength in a direction (the first direction) parallel to the planar portion 10s of the substrate 10. In the period P1, the width W1 of a single body of the first protrusion 11 in the first direction (the horizontal direction in FIG. 1B) and the distance W2 between two of the first protrusions 11 that are adjacent to each other are added together (P1=W1+W2). In addition, the first protrusion 11 is in a rectangular convex shape in the cross-sectional view, and a plurality of the first protrusions 11 is formed in a line and space (a stripe shape) in the plan view.

It is preferable that, for example, the period P1 of the first protrusions 11 is set in the range of 100 nm to 1000 nm, and the height T1 of the first protrusions 11 is set in the range of 10 nm to 100 nm. Accordingly, the first protrusions 11 can serve as a structure for implementing the LSPR.

The width W1 of the first protrusion 11 in the first direction is greater than the distance W2 between two of the first protrusions 11 that are adjacent to each other (W1>W2). Accordingly, the spatial filling rate of the first protrusions 11 in which the LSPR is excited increases.

Two or more second protrusions 12 are formed on the upper face 11a of each of the plurality of the first protrusions 11 so as to have a predetermined height T2. More specifically, the second protrusions 12 are not formed on the base portion 10a (the planar portion 10s of the substrate 10 in an area between two of the first protrusions 11 that are adjacent to each other) of the substrate 10 but are formed only on the upper face 11a of the first protrusion 11.

These second protrusions 12 are arranged in a period P2 that is shorter than the light wavelength in a direction (the third direction) parallel to the planar portion 10s of the substrate 10. In the period P2, the width of a single body of the second protrusion 12 in the third direction (the horizontal direction in FIG. 1B) and the distance between two of the second protrusions 12 that are adjacent to each other are added together. Accordingly, the period P2 of the second protrusions 12 is sufficiently shorter than the period P1 of the first protrusions 11.

It is preferable that, for example, the period P2 of the second protrusions 12 is set to a value less than 500 nm, and the height T2 of the second protrusions 12 is set to a value less than 200 nm. Accordingly, the second protrusions 12 can serve as a structure for implementing the SERS.

In this embodiment, the arrangement direction (the first direction) of the first protrusions 11 and the arrangement direction (the third direction) of the second protrusions 12 are the same. In addition, second protrusion 12, similarly to the first protrusion 11, is in a rectangular convex shape in the cross-sectional view, and a plurality of the second protrusions 12 is formed as a line and space (a stripe shape) in the plan view.

As metal of the surface of the diffraction grating 9, for example, gold (Au), silver (Ag), copper (Cu), aluminum (Al), or an alloy thereof is used. In this embodiment, gold or silver that has a characteristic of exhibiting the SPP, the LSPR, and the SERS is used. Accordingly, the SPP, the LSPR, and the SERS can be easily exhibited, and a target substance can be detected with high sensitivity.

Here, the SPP, the LSPR, and the SERS will be described. When light is incident to the surface of the sensor chip 1, that is, the face on which the plurality of the first protrusions 11 and the plurality of the second protrusions 12 are formed, a surface-specific oscillation mode (surface plasmon) caused by the plurality of the first protrusions 11 is generated. However, the polarized state of the incident light is TM (Transverse Magnetic) polarized light that is perpendicular to the groove direction of the first protrusions 11. Then, the oscillation of an electromagnetic wave is excited accompanying the oscillation of free electrons. Since the oscillation of the free electrons is influenced by this oscillation of the electromagnetic wave, a system acquired by combining both the oscillations, that is, a so-called surface plasmon polariton (SPP) is generated. In this embodiment, the incident angle of light is approximately vertical with respect to the surface of the chip. However, the incident angle is not limited to this angle (vertical), as long as it satisfies the conditions for exciting the SPP.

This SPP propagates along the surface of the sensor chip 1, and more specifically, along an interface between the air and the second protrusion 12 and excites a localized electromagnetic field near the second protrusion 12. The coupling of the SPP is sensitive to the light wavelength, and the coupling efficiency is high. As described above, localized surface plasmon resonance (LSPR) can be excited from the incident light that is in the air propagation mode through the SPP. Then, from the relationship between the LSPR and Raman scattering light, surface enhanced Raman scattering (SERS) can be used.

Figure 2A:
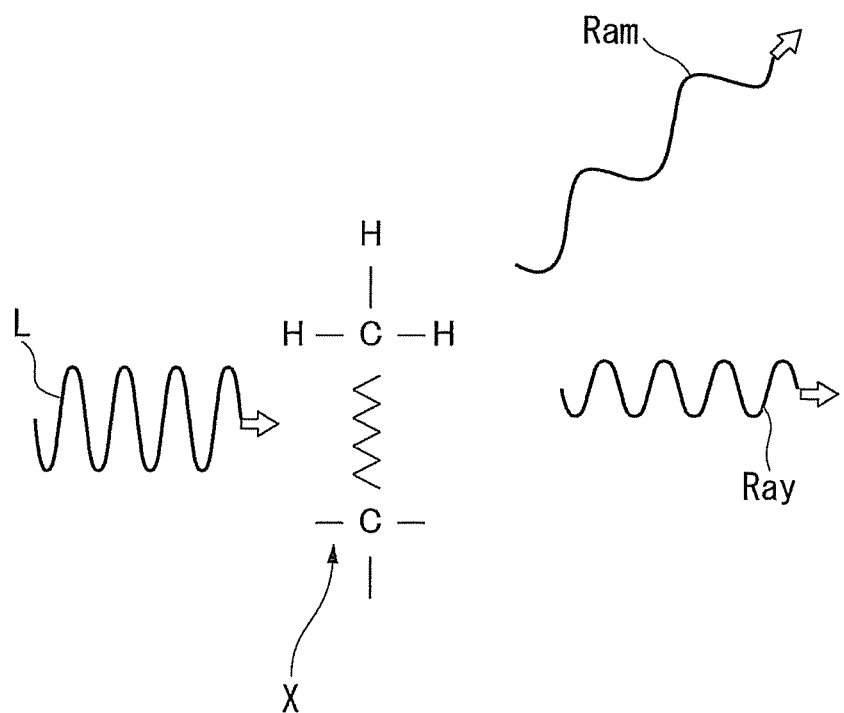
FIGS. 2A and 2B are diagrams representing a Raman scattering spectroscopy.
Figure 2B:
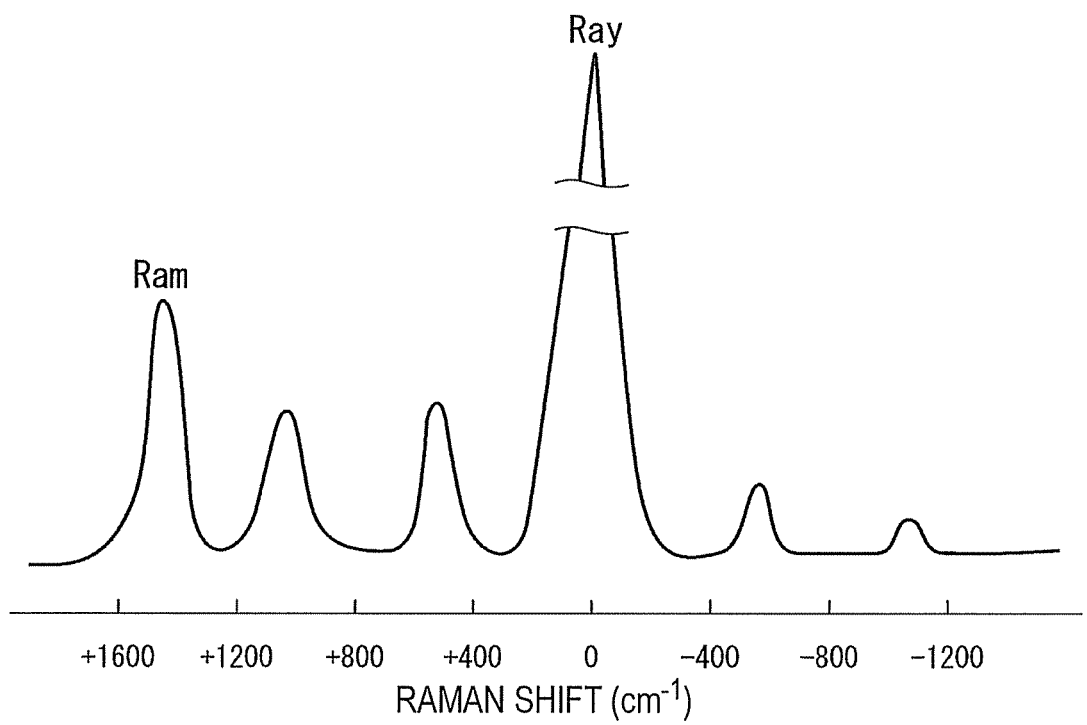

FIGS. 2A and 2B are diagrams representing a Raman scattering spectroscopy. FIG. 2A represents the principle of the Raman scattering spectroscopy. In addition, FIG. 2B represents a Raman spectrum (the relationship between a Raman shift and the intensity of Raman scattering). In FIG. 2A, reference sign L represents incident light (light of a single wavelength), reference sign Ram represents Raman scattering light, reference sign Ray represents Rayleigh scattering light, and reference sign X represents a target molecule (target substance). In FIG. 2B, the horizontal axis represents the Raman shift. Here, the Raman shift is the difference between the frequency of the Raman scattering light Ram and the frequency of the incident light L and has a value that is specific to the structure of the target molecule X.

As shown in FIG. 2A, when light L of a single wavelength is emitted to the target molecule X, light having a wavelength different from that of the incident light is generated in the scattering light (Raman scattering light Ram). The difference between the energy levels of the Raman scattering light Ram and the incident light L corresponds to the energy of the oscillation level, the rotation level, or the electron levels of the target molecule X. The target molecule X has an oscillation energy level that is specific to the structure thereof, and accordingly, the target molecule X can be specified by using the light L of a single wavelength.

For example, when the oscillation energy of the incident light L is denoted by V1, the oscillation energy consumed by the target molecule X is denoted by V2, and the oscillation energy of the Raman scattering light Ram is denoted by V3, V3=V1−V2. After colliding with the target molecule X, most of the incident light L has energy with the same magnitude as that of energy before the collision. This elastic scattering light is termed Rayleigh scattering light Ray. For example, when the oscillation energy of the Rayleigh scattering light Ray is denoted by V4, V4=V1.

From the Raman spectrum shown in FIG. 2B, it can be understood that the Raman scattering light Ram is weak by comparing the scattering intensity (spectrum peak) of the Raman scattering light Ram and the scattering intensity of the Rayleigh scattering light Ray. As described above, the Raman scattering spectroscopy is a measurement technique that has a superior capability for identifying a target molecule X and low sensitivity for sensing a target molecule X. Accordingly, in this embodiment, in order to increase the sensitivity, spectroscopy using the surface enhanced Raman scattering (SERS spectroscopy) is used (see FIG. 4).

Figure 3A:
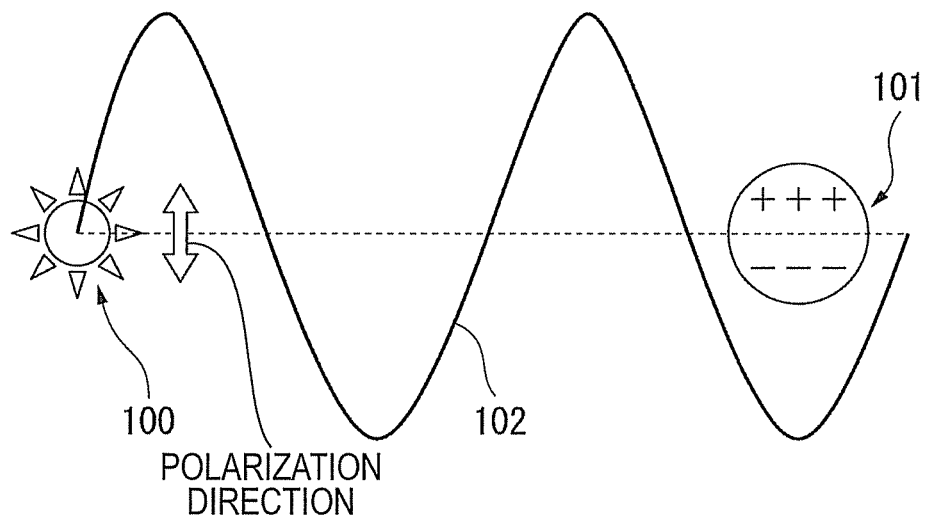
FIGS. 3A and 3B are diagrams representing an electric field enhancing mechanism using LSPR.
Figure 3B:
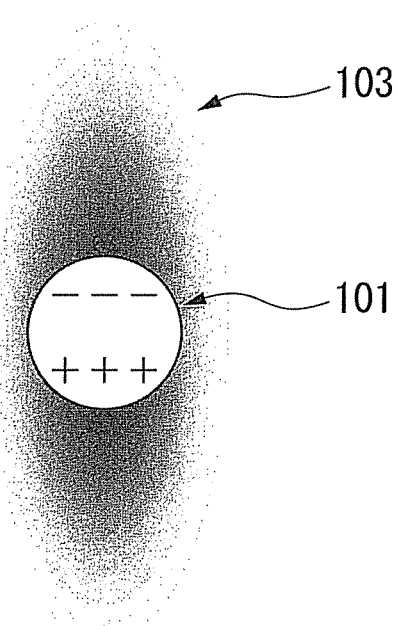

FIGS. 3A and 3B are diagrams representing an electric field enhancing mechanism using the LSPR. FIG. 3A is a schematic diagram representing a state when light is incident to a metal nanoparticle. FIG. 3B is a diagram representing an LSPR enhanced electric field. In FIG. 3A, reference sign 100 represents a light source, reference sign 101 represents a metal nanoparticle, and reference sign 102 represents light emitted from the light source. In FIG. 3B, reference sign 103 represents a surface localized electric field.

As shown in FIG. 3A, when the light 102 is incident to the metal nanoparticle 101, free electrons are in a state of resonant oscillation accompanying the oscillation of the light 102. The particle diameter of the metal nanoparticle is smaller than the wavelength of the incident light. For example, the light wavelength is in the range of 400 nm to 800 nm, and the particle diameter of the metal nanoparticle is in the range of 10 nm to 100 nm. As the metal nanoparticle, Ag or Au is used.

Then, a strong surface localized electric field 103 is excited near the metal nanoparticle 101 accompanying the resonant oscillation of the free electrons (see FIG. 3B). As above, the LSPR can be excited by allowing the light 102 to be incident to the metal nanoparticle 101.

Figure 4:
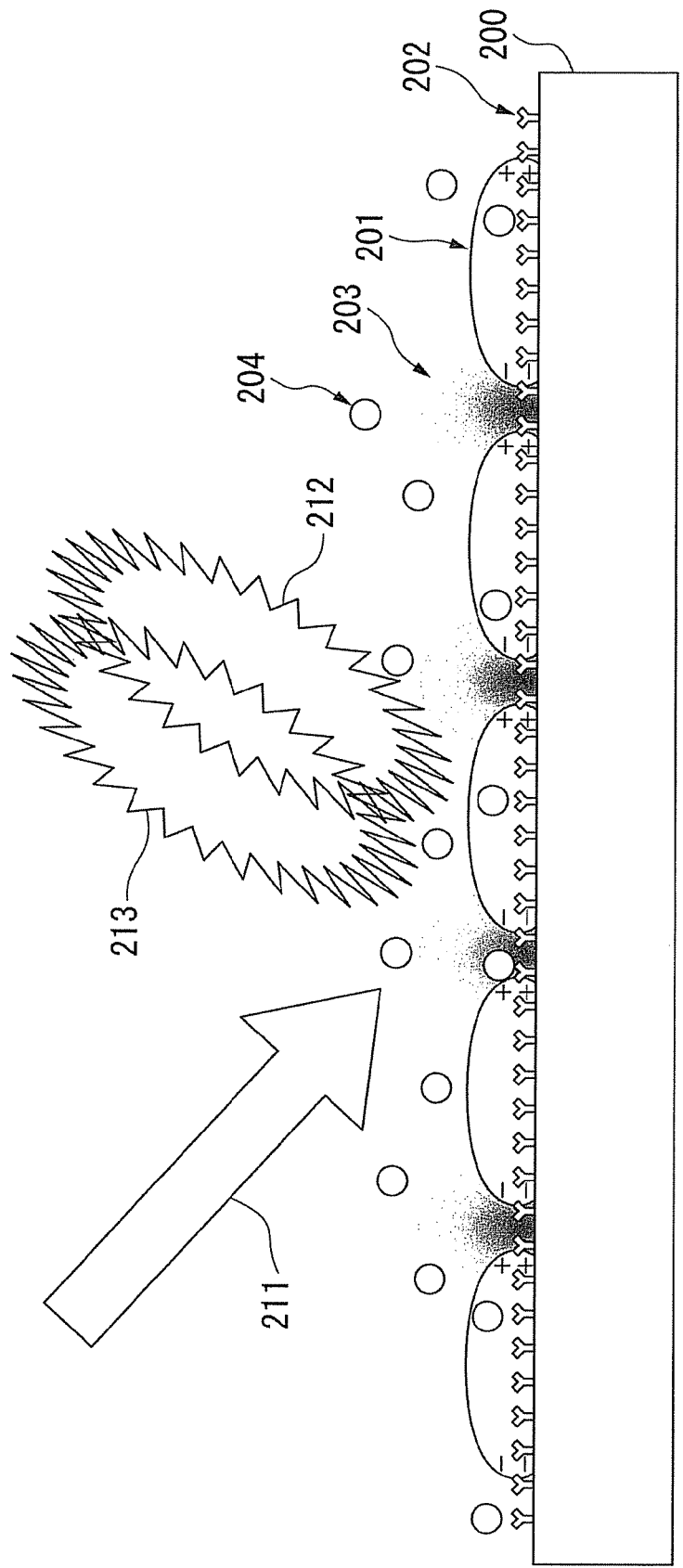
FIG. 4 is a diagram representing the SERS spectroscopy.

FIG. 4 is a diagram representing the SERS spectroscopy. In FIG. 4, reference sign 200 represents a substrate (corresponding to the first protrusion according to an embodiment of the invention), reference sign 201 represents a metal nanostructure (corresponding to the second protrusion according to an embodiment of the invention), reference sign 202 represents a selective adsorption film, reference sign 203 represents an enhanced electric field, reference sign 204 represents a target molecule, reference sign 211 represents an incident laser beam, reference sign 212 represents Raman scattering light, and reference sign 213 represents Rayleigh scattering light. The selective adsorption film 202 adsorbs the target molecule 204.

As shown in FIG. 4, when the laser beam 211 is incident to the metal nanostructure 201, free electrons are in a state of resonant oscillation accompanying the oscillation of the laser beam 211. The size of the metal nanostructure 201 is smaller than the wavelength of the incident laser beam. Then, accompanying the resonant oscillation of the free electrons, a strong surface localized electric field is excited near the metal nanostructure 201. Accordingly, the LSPR is excited. When the distance between the metal nanostructures 201 that are adjacent to each other decreases, an extremely strong enhanced electric field 203 is generated near the contact point. When one to several target molecules 204 are adsorbed on the contact points, the SERS is generated from the contact points. This point is also checked by the result of an enhanced electric field generated between two adjacent silver nanoparticles that is calculated by using a finite difference time domain (FDTD) method. Accordingly, by performing selective spectroscopy for the Raman scattering light, the target molecule can be detected with high sensitivity.

This embodiment, as described above, has a structure in which the LSPR is excited by arranging the first protrusions 11 in the period P1 shorter than the light wavelength in the direction parallel to the planar portion of the substrate 10. In addition, this embodiment has a structure in which the SERS is exhibited by forming two or more of the second protrusions 12 on only the upper face 11a of the first protrusion 11. More specifically, when light of a single wavelength is emitted to a target molecule, based on the principle of generating the Raman scattering light, an enhanced magnetic field is generated near the contact point by disposing the target molecules between two of the second protrusions 12 that are adjacent to each other, whereby the SERS is generated. Accordingly, it is possible to use the SERS spectroscopy capable of detecting a target substance with sensitivity that is higher than that of the Raman scattering spectroscopy.

Figure 5:
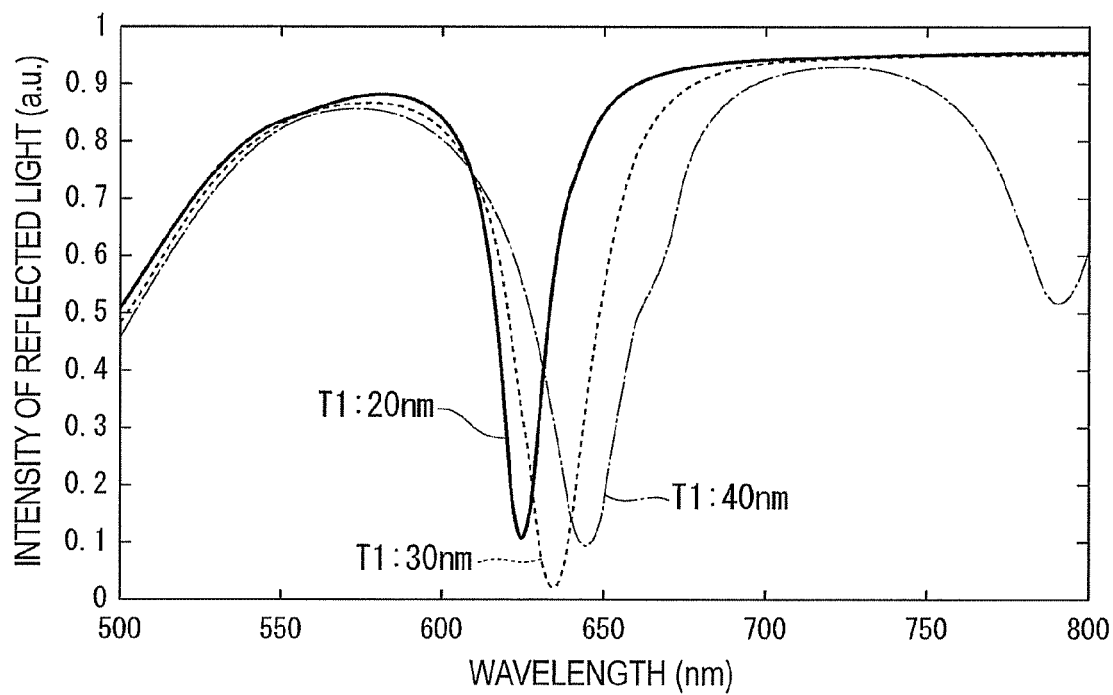
FIG. 5 is a graph representing the intensity of reflected light reflected from a single body of the first protrusion.

FIG. 5 is a graph representing the intensity of reflected light reflected from a single body of the first protrusion. In FIG. 5, the horizontal axis represents the light wavelength, and the vertical axis represents the intensity of the reflected light. The height T1 of the first protrusion 11 is taken as a parameter (T1=20 nm, 30 nm, and 40 nm). In addition, in the structure of the sensor chip 1 according to this embodiment, a value calculated by subtracting the intensity of the reflected light from the intensity of the incident light (assumed to be 1.0) is absorbance.

The light is incident vertically to the first protrusion 11. The polarization direction of the light is TM polarized light. The period of the first protrusions 11 is 580 nm, and the resonant peak of the intensity of the reflected light is a wavelength in the region of 630 nm. This resonant peak originates from the SPP, and as the height T1 of the first protrusion 11 is increased, the resonant peak is shifted to the longer wavelength side (the long wavelength region). When the height T1 of the first protrusion 11 is 30 nm, the intensity of the reflected light is the highest, and accordingly, it can be understood that the absorption strength appears to be the strongest.

Figure 6:
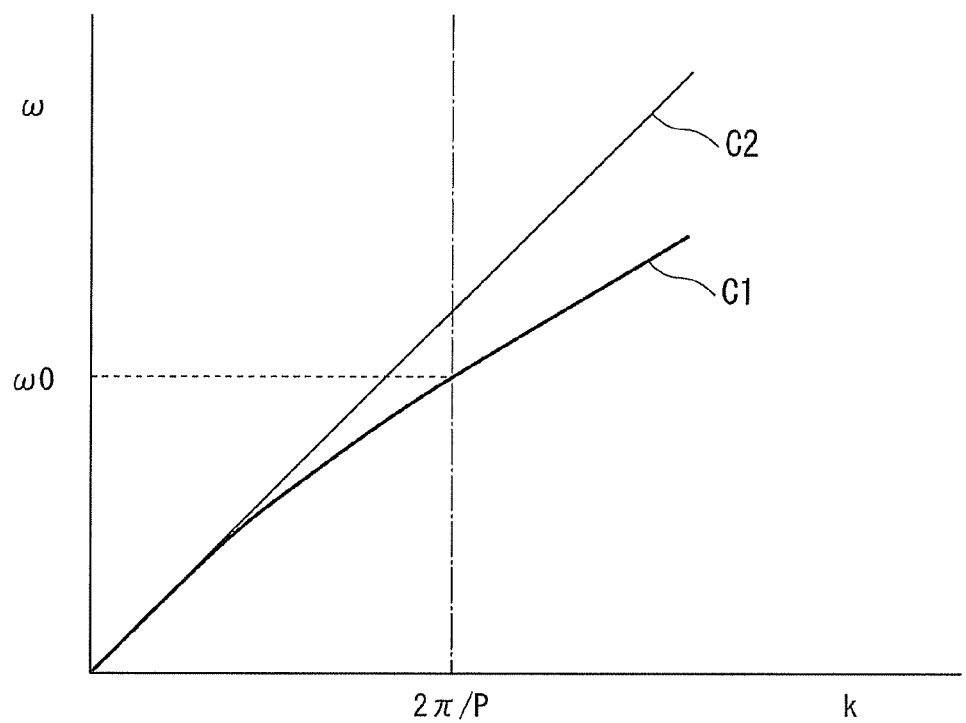
FIG. 6 is a graph representing the dispersion curve of SPP.

FIG. 6 is a graph representing the dispersion curve of the SPP. In FIG. 6, reference sign C1 represents a dispersion curve (as an example, it represents a value at the interface of the air and Au) of the SPP, and reference sign C2 represents a light line. The period of the first protrusion 11 is 580 nm. The position of the lattice vector of the first protrusion 11 is shown on the horizontal axis (corresponding to 2π/P on the horizontal axis shown in FIG. 6). When a line extends from this position toward the upper side, the line intersects the dispersion curve of the SPP. The wavelength corresponding to this intersection is acquired by using the following equation.

$$\lambda = P1 \sqrt{\frac{E1 \cdot E2}{E1 + E2}} \quad (1)$$

In Equation (1), P1 represents the period of the first protrusions 11, E1 represents the complex permittivity of the air, and E2 represents the complex permittivity of Au. By substituting P1, E1, and E2 with respective values in Equation (1), λ=620 nm is acquired (corresponding to w0 on the vertical axis shown in FIG. 6).

As the height T1 of the first protrusion 11 is increased, the imaginary part of the wave number of the SPP increases. Accordingly, the real part of the wave number of the SPP decreases, whereby the intersection of the line extended from the position of the lattice vector and the dispersion curve of the SPP moves from the upper right side to the lower left side. In other words, the resonant peak is shifted to the longer wavelength side.

Figure 7:
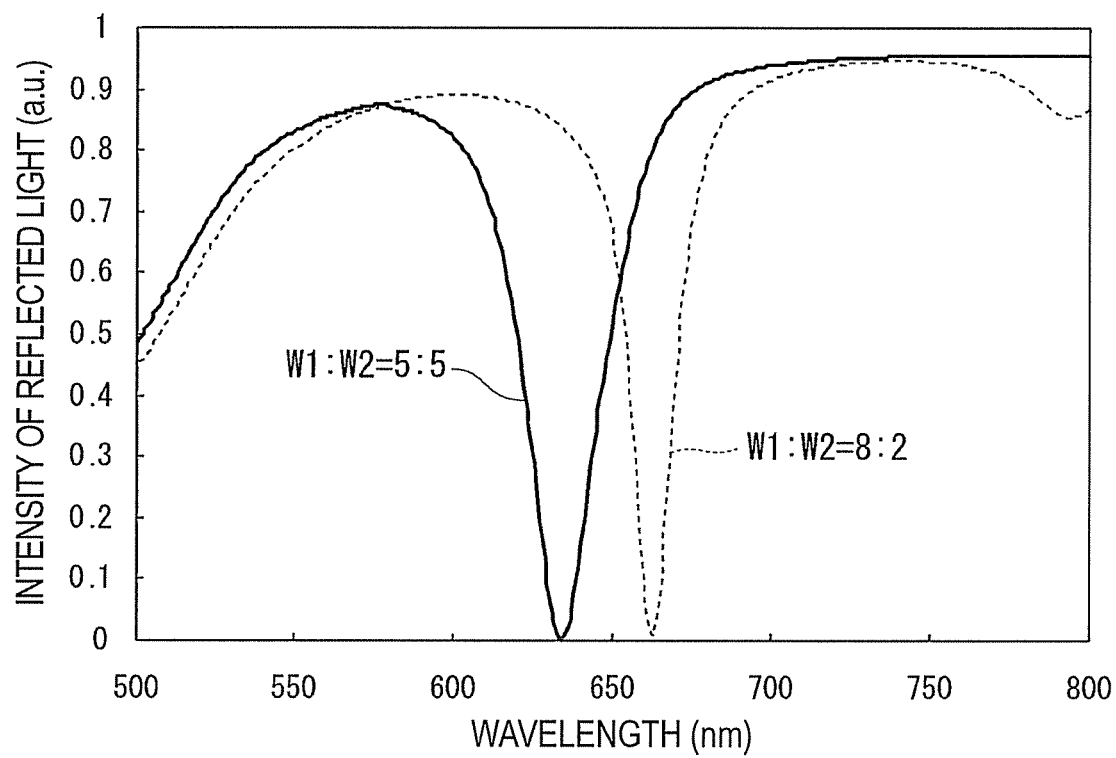
FIG. 7 is a graph representing the intensity of reflected light reflected from the single body of the first protrusion.

FIG. 7 is a graph representing the intensity of the reflected light reflected from the single body of the first protrusion. In FIG. 7, the horizontal axis represents the light wavelength, and the vertical axis represents the intensity of the reflected light. A ratio (hereinafter, referred to as a duty ratio) of the width W1 of the first protrusion 11 in the first direction to a distance W2 between two of the first protrusions adjacent to each other is taken as a parameter (W1:W2=5:5 and W1:W2=8:2). In addition, the graph of the parameter W1:W5=5:5 in this figure is the same as the graph of the parameter T1=30 shown in FIG. 5.

The TM polarized light is incident vertically to the first protrusion 11. When the period of the first protrusions 11 is 580 nm and the duty ratio is W1:W2=5:5, the resonant peak of the intensity of the reflected light is a wavelength in the region of 630 nm. In addition, when the duty ratio is W1:W2=8:2, the resonant peak of the intensity of the reflected light is a wavelength in the region of 660 nm. When the duty ratio is increased, the gradient of the resonant peak is sharpened, and accordingly, the resonant peak is shifted to the longer wavelength side.

Figure 8A:
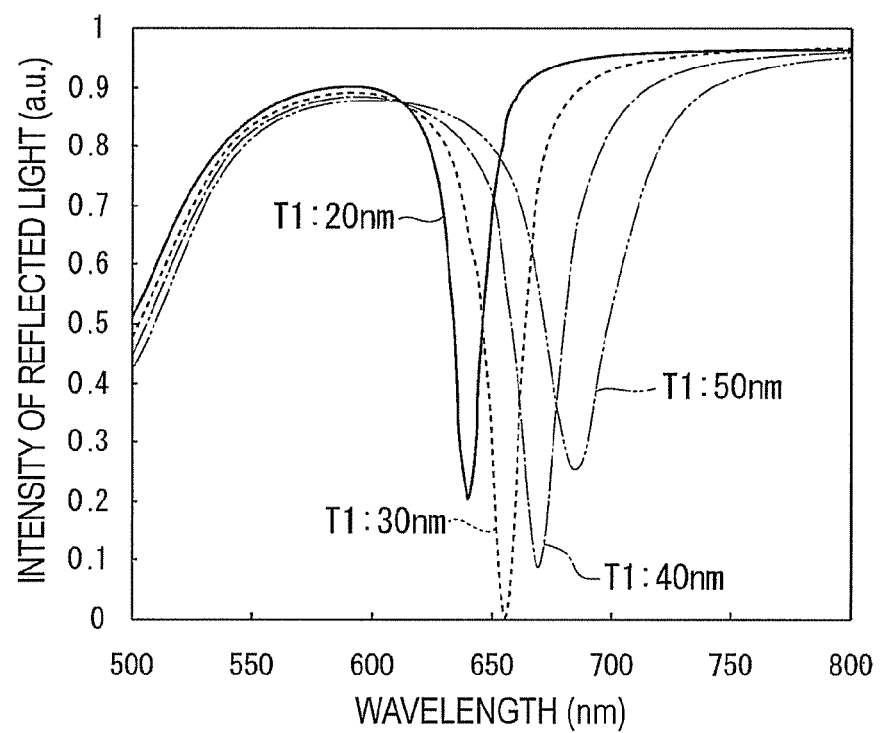
FIGS. 8A and 8B are graphs representing the intensities of the reflected light reflected from the single body of the first protrusion.
Figure 8B:
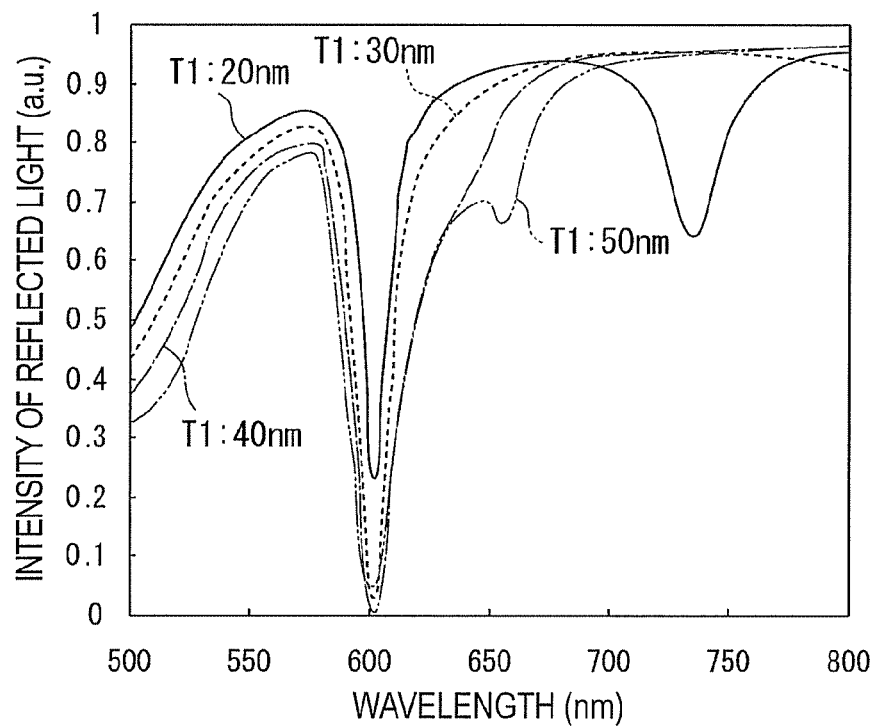
Figure 9A:
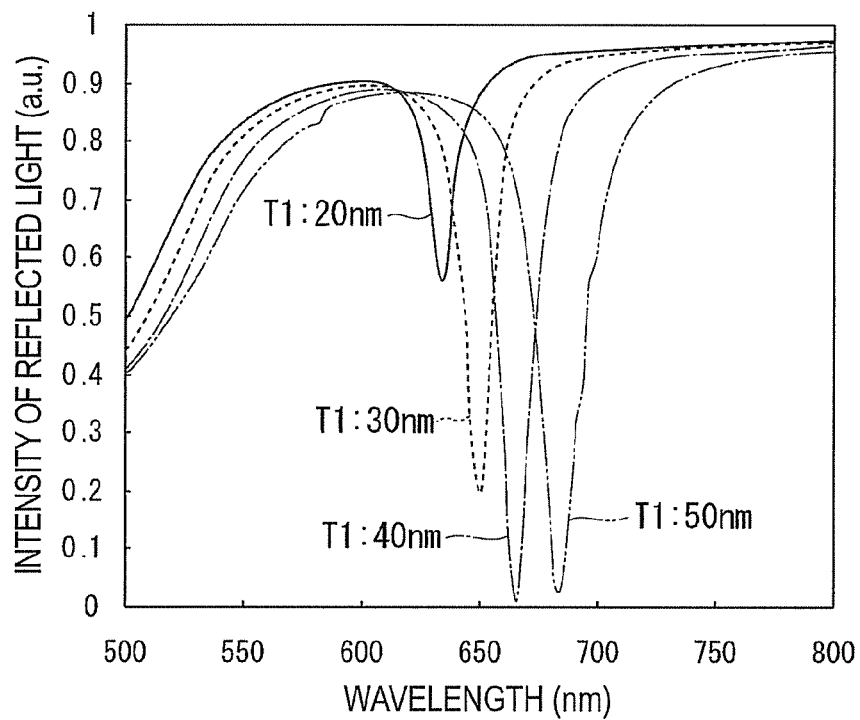
FIGS. 9A and 9B are graphs representing the intensities of the reflected light reflected from the single body of the first protrusion.
Figure 9B:
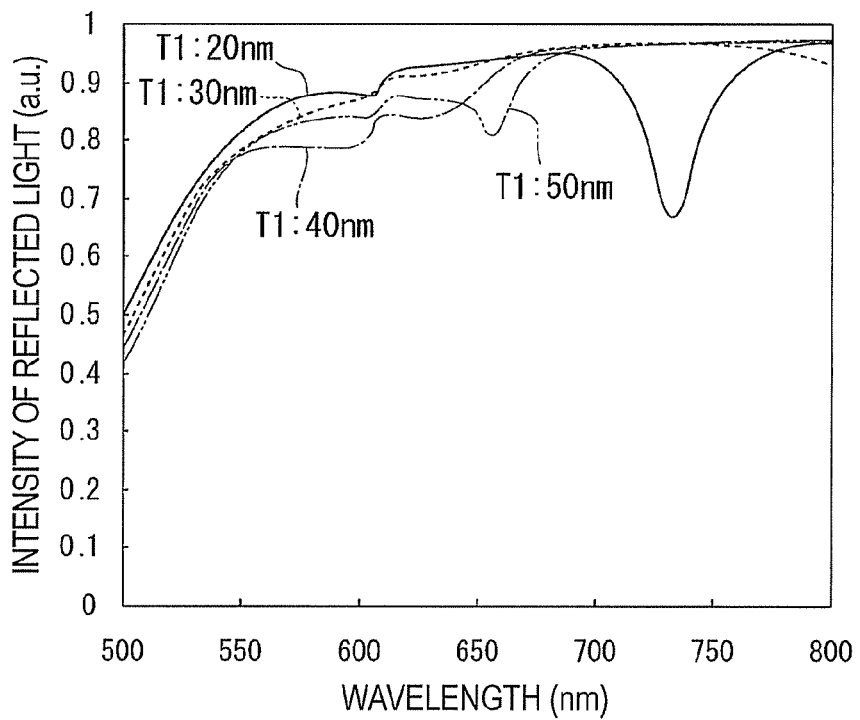

FIGS. 8A to 9B are graphs representing the intensities of the reflected light reflected from the single body of the first protrusion. FIG. 8A is a graph in a case where the duty ratio is W1:W2=7:3. FIG. 8B is a graph in a case where the duty ratio is W1:W2=3:7. FIG. 9A is a graph in a case where the duty ratio is W1:W2=9:1. FIG. 9B is a graph in a case where the duty ratio is W1:W2=1:9. In FIGS. 8A to 9B, the horizontal axis represents the light wavelength, and the vertical axis represents the intensity of reflected light. The height T1 of the first protrusion 11 is taken as a parameter (T1=20 nm, 30 nm, 40 nm, or 50 nm).

The TM polarized light is incident vertically to the first protrusion 11. In a case where the duty ratio of the first protrusion 11 is W1:W2=7:3, and the height T1 is 30 nm, the resonant peak of the intensity of the reflected light is a wavelength in the region of 660 nm (see FIG. 8A). On the other hand, in a case where the duty ratio is W1:W2=3:7, and the height T1 is 40 nm, the resonant peak of the intensity of the reflected light is a wavelength in the region of 600 nm (see FIG. 8B). In the case where the duty ratio of the first protrusion 11 is W1:W2=7:3, it can be understood that the position of the resonant peak of the intensity of the reflected light is shifted to the longer wavelength side as the height T1 is increased. However, in the case where the duty ratio of the first protrusion 11 is W1:W2=3:7, it can be understood that the position of the resonant peak of the intensity of the reflected light hardly changes.

In a case where the duty ratio of the first protrusion 11 is W1:W2=9:1, and the height T1 is 40 nm, the resonant peak of the intensity of the reflected light is a wavelength in the region of 670 nm (see FIG. 9A). On the other hand, in a case where the duty ratio is W1:W2=1:9, and the height T1 is 20 nm, the resonant peak of the intensity of the reflected light is a wavelength in the region of 730 nm, and the gradient of the resonant peak is broad (see FIG. 9B). In the case where the duty ratio of the first protrusion 11 is W1:W2=9:1, it can be understood that the position of the resonant peak of the intensity of the reflected light is shifted to the longer wavelength side as the height T1 is increased. However, in the case where the duty ratio of the first protrusion 11 is W1:W2=1:9, the resonant peak of the intensity of the reflected light is small.

Figure 10:
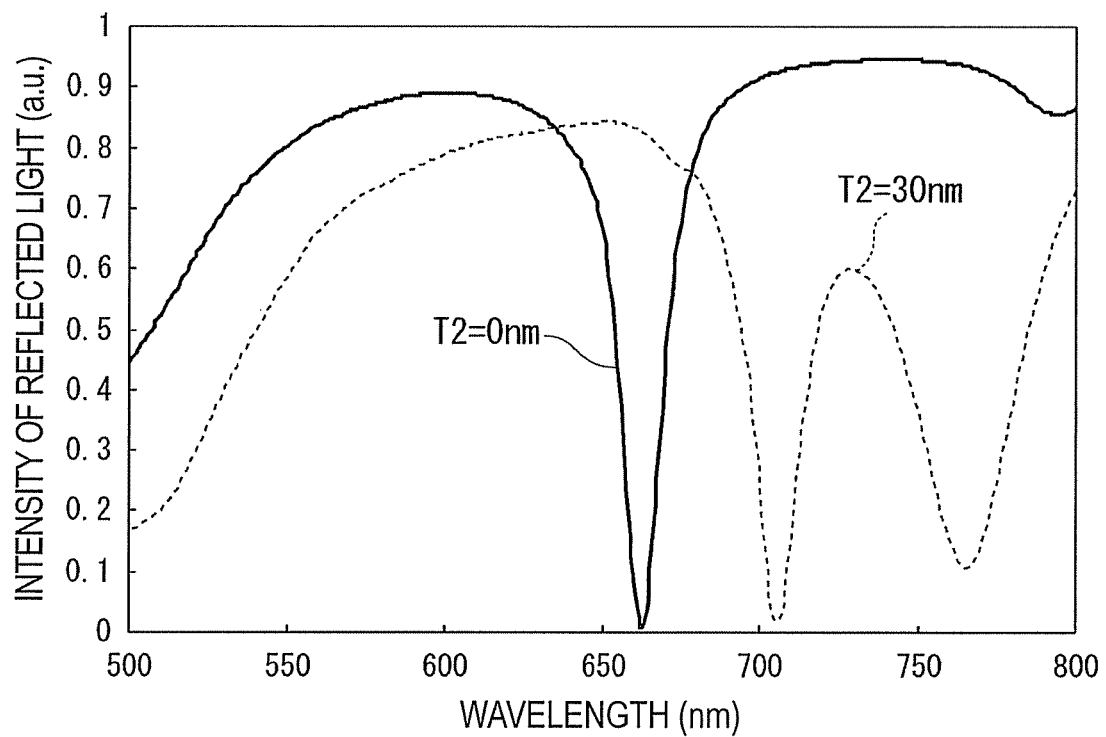
FIG. 10 is a graph representing the intensity of reflected light of a sensor chip according to an embodiment of the invention.

FIG. 10 is a graph representing the intensity of reflected light of a structure in which the second protrusions 12 are superimposed on the first protrusion 11, that is, the sensor chip 1 according to an embodiment of the invention. In FIG. 10, the horizontal axis represents the light wavelength, and the vertical axis represents the intensity of reflected light. The height T2 of the second protrusion 12 is taken as a parameter (T2=0 nm and 30 nm). The graph of the parameter T2=0 in this figure is the same as the graph of the parameter W1:W2=8:2 shown in FIG. 7.

The TM polarized light is incident vertically to the first protrusion 11. The duty ratio of the first protrusion 11 is W1:W2=8:2, and the height T1 of the first protrusion 11 is 30 nm. In addition, the period P2 of the second protrusion 12 is 116 nm. By forming a plurality of the second protrusions 12 on only the upper face 11a of the first protrusion 11, the position of the resonant peak of the intensity of the reflected light is shifted from a wavelength 660 nm to a position in the region of a wavelength of 710 nm. In addition, the sharpness and the gradient of the resonant peak are maintained. This resonant peak originates from the above-described SERS. In a case where the height T2 of the second protrusion 12 is 30 nm, a strong localized electric field can be excited near the surface of the second protrusion 12 by emitting light with a wavelength of 710 nm. In addition, by appropriately changing the periods P1 and P2 and the heights T1 and T2 of the first protrusion 11 and the second protrusion 12, the position of the resonant peak can be adjusted to an arbitrary wavelength.

Figure 11A:
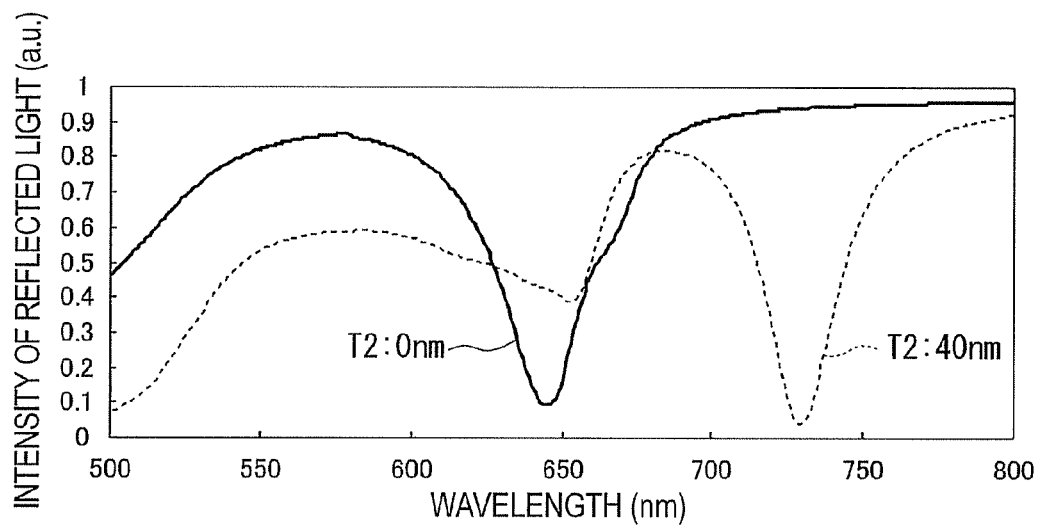
FIGS. 11A to 11C are graphs representing the intensities of the reflected light of a structure in which the second protrusion is superimposed on a planar portion of a substrate.
Figure 11B:
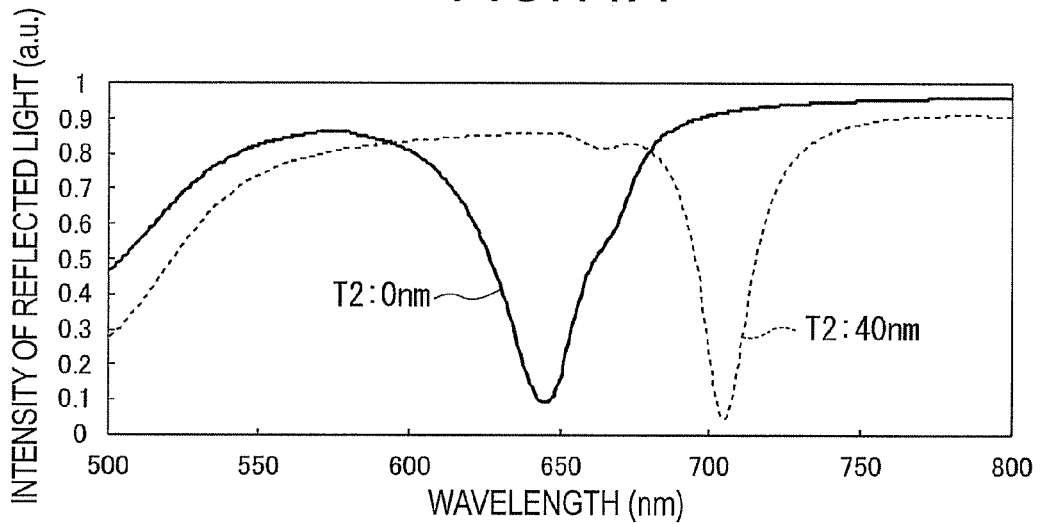
Figure 11C:
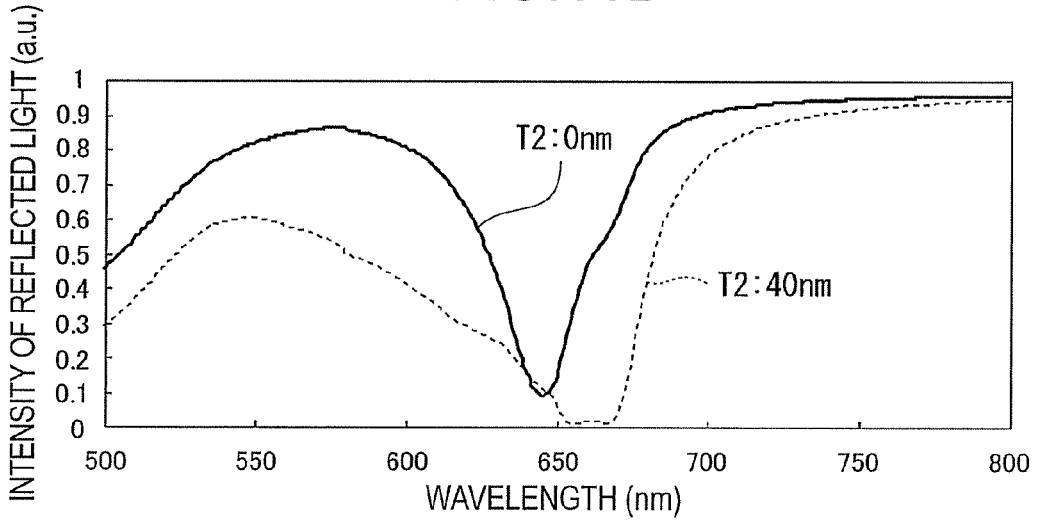

FIGS. 11A to 11C are graphs representing the intensities of the reflected light of a structure in which the second protrusion 12 is superimposed on the substrate 10. FIG. 11A is a graph in a case (not shown in the figure) where a plurality of the second protrusions is formed on the upper face of the first protrusion and the planar portion of the substrate (the base portion of the substrate) in an area between two of the first protrusions adjacent to each other. FIG. 11B is a graph in a case where a plurality of the second protrusions is formed on only the upper face of the first protrusion (the structure of a sensor chip according to an embodiment of the invention). FIG. 11C is a graph in a case where a plurality of the second protrusions is formed on only the planar portion of the substrate (the base portion of the substrate) in an area between two of the first protrusions adjacent to each other. In FIGS. 11A to 11C, the horizontal axis is the light wavelength, and the vertical axis is the intensity of reflected light. The height T2 of the second protrusion 12 is taken as a parameter (T2=0 nm and 40 nm). The graph of parameter T2=0 in this figure is the same as the graph of the parameter T1=30 shown in FIG. 5.

The TM polarized light is incident vertically to the first protrusion 11. The period of the first protrusions 11 is 580 nm, the duty ratio of the first protrusion 11 is W1:W2=5:5, and the height T1 of the first protrusion 11 is 30 nm. In addition, the period P2 of the second protrusion 12 is 97 nm, and the height T2 of the second protrusion 12 is 40 nm.

It can be understood that the position of the resonant peak of the intensity of the reflected light is shifted from a wavelength 640 nm to a position in the region of a wavelength of 730 nm by forming a plurality of the second protrusions on each of the upper face of the first protrusion and the base portion of the substrate (see FIG. 11A). In addition, it can be understood that the position of the resonant peak of the intensity of the reflected light is shifted from a wavelength 640 nm to a position in the region of a wavelength of 710 nm by forming a plurality of the second protrusions 12 on only the upper face 11a of the first protrusion 11 (see FIG. 11B). However, it can be understood that the position of the resonant peak of the intensity of the reflected light hardly changes even in a case where a plurality of the second protrusions is formed on only the base portion of the substrate.

From these results, the SPP is thought to propagate mainly along the interface between the air and the upper face of the first protrusion. Accordingly, a structure in which the second protrusion is not formed on the base portion of the substrate, and two or more second protrusions are formed on only the upper face of the first protrusion is effective as a structure for further exhibiting the SERS by exciting the LSPR. By setting the duty ratio of the first protrusion to be relatively large (W1>W2), the spatial filling rate of the first protrusion that excites the LSPR increases. Accordingly, the energy of light emitted when specifying a target substance can be effectively used.

Figure 12:
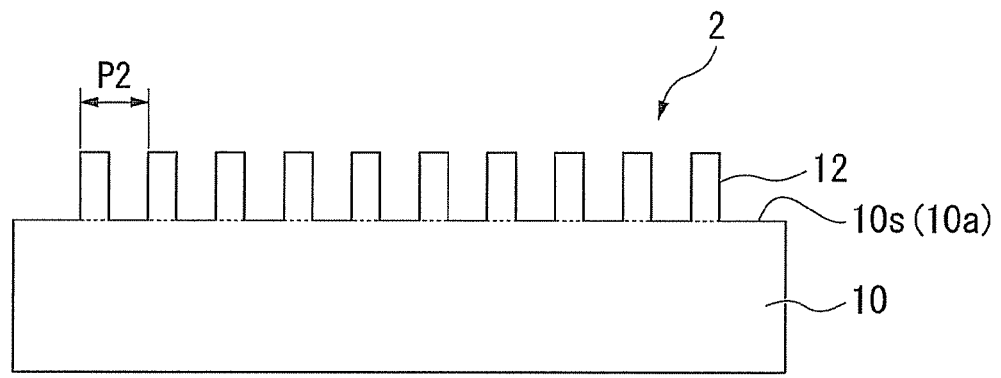
FIG. 12 is a schematic diagram of a sensor chip in which a plurality of the second protrusions is formed in the planar portion of the substrate.

FIG. 12 is a diagram schematically showing the sensor chip 2 in a case where the first protrusion 11 is not formed in the planar portion 10s of the substrate 10, and only the second protrusions 12 are formed on the planar portion 10s of the substrate 10, that is, a case where a plurality of the second protrusions 12 is formed in the planar portion 10s of the substrate 10.

Figure 13:
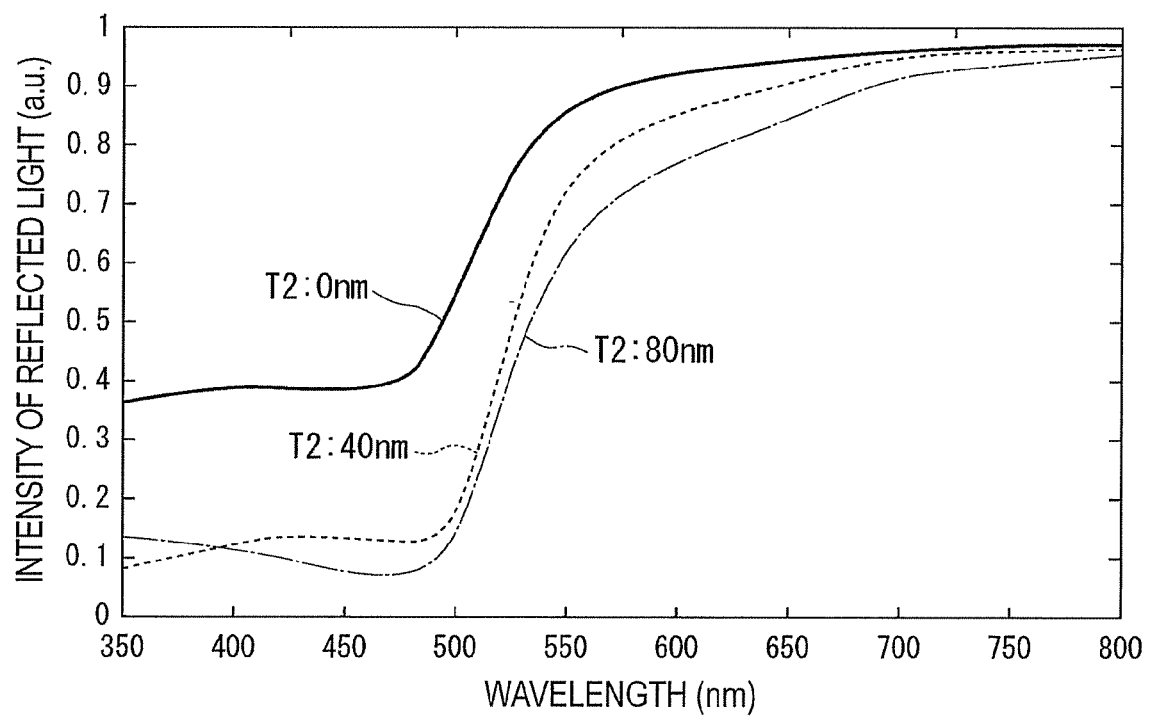
FIG. 13 is a graph representing the intensity of reflected light of a sensor chip shown in FIG. 12.

FIG. 13 is a graph representing the intensity of reflected light of a sensor chip 2 in a case where a plurality of the second protrusions is formed on the planar portion 10s of the substrate 10. In FIG. 13, the horizontal axis represents the light wavelength, and the vertical axis represents the intensity of the reflected light. The height T2 of the second protrusion 12 is taken as a parameter (T2=0 nm, 40 nm, and 80 nm). The TM polarized light is incident vertically to the second protrusion 12. By referring to figure, the resonant peak of the intensity of the reflected light is not recognized. From this result, it can be understood that light energy cannot be coupled with the second protrusion 12 in a case where there is no first protrusion 11, that is, not through the SPP.

FIGS. 14A to 14F are diagrams representing the manufacturing process of the sensor chip. First, an Au film 31 is formed on a glass substrate 30 by using a method such as a deposition method or a sputtering method. Next, the upper face of the Au film 31 is coated with a resist 32 by using a method such as a spin coat method (see FIG. 14A). At this time, the Au film 31 is formed so as to have a film thickness Ta for which incident light is not transmitted (for example, 200 nm).

Figure 14A:
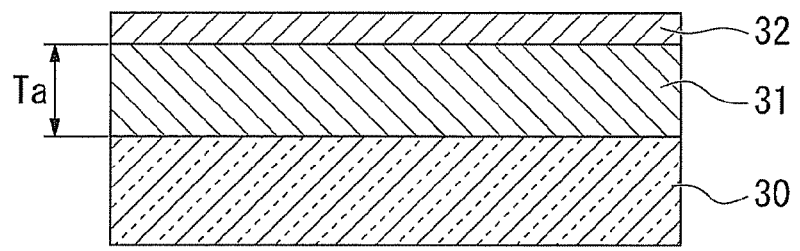
FIGS. 14A to 14F are diagrams representing the manufacturing process of the sensor chip.
Figure 14B:
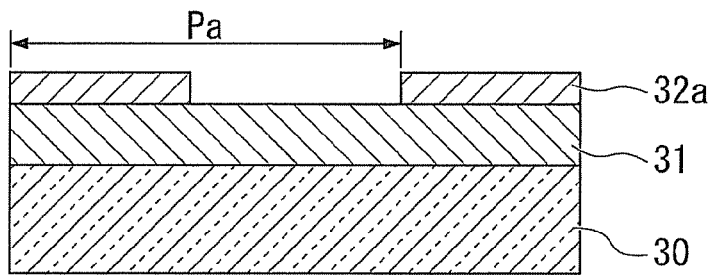
Figure 14C:
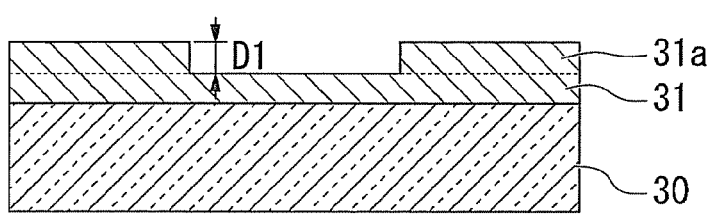

Next, a resist pattern 32a is formed in a period Pa of 580 nm by using a method such as an imprint method (see FIG. 14B). Next, the Au film 31 is etched by a predetermined depth D1 (for example, 70 nm) by performing dry etching by using the resist pattern 32a as a mask. Thereafter, by removing the resist pattern 32a, the first protrusion 31a is formed (see FIG. 14C).

Figure 14D:
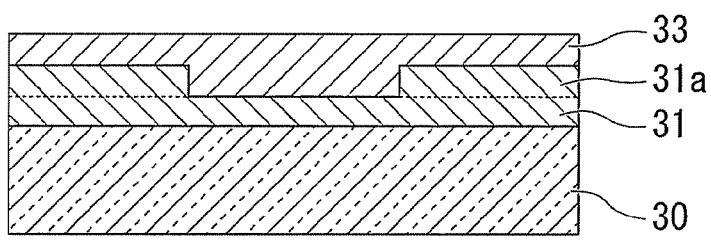
Figure 14E:
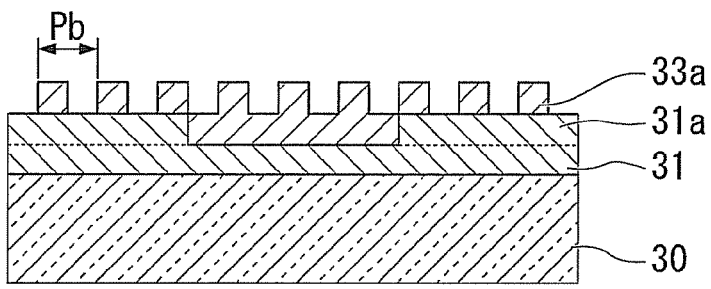
Figure 14F:
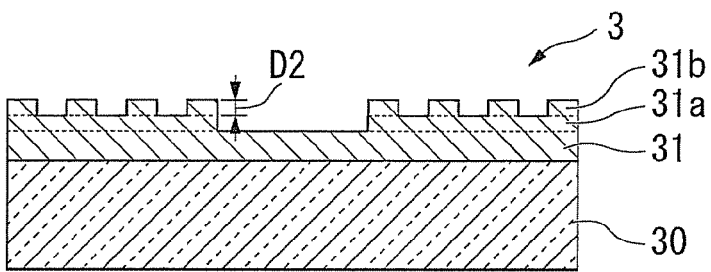

Next, the upper face of the Au film 31 on which the first protrusion 31a is formed is coated with a resist 33 by using a method such as a spin coat method (see FIG. 14D). Next, resist patterns 33a is formed in a period Pb of 116 nm on only the upper face of the first protrusion 31a by using a method such as an imprint method (see FIG. 14E). Next, only the first protrusion 31a is etched by a predetermined depth D2 (for example, 40 nm) by performing dry etching by using the resist patterns 33a as a mask. Thereafter, the second protrusion 31b is formed by removing the resist patterns 33a (see FIG. 14F). By performing the above-described processes, a sensor chip 3 according to an embodiment of the invention can be manufactured.

In the sensor chip 1 according to an embodiment of the invention, the LSPR is excited through the SPP by a metallic microstructure due to the first protrusion 11, and the SERS can be further exhibited by a metallic microstructure due to the second protrusion 12. More specifically, when light is incident to a face on which a plurality of the first protrusions 11 and a plurality of the second protrusions 12 are formed, an oscillation mode (surface plasmon) specific to the surface of the plurality of the first protrusions 11 is generated. Then, free electrons are in a state of resonant oscillation accompanying the oscillation of light so as to excite the SPP, whereby a strong surface localized electric field is excited near the plurality of the second protrusions 12. Accordingly, the LSPR is excited. In this structure, since a distance between two of the second protrusions 12 adjacent to each other is short, an extremely strong enhanced electric field is generated near the contact points. Then, when one to several target substances are adsorbed to the contact points, the SERS is generated from the contact points. Accordingly, the intensity characteristics in which the width of the spectrum of the intensity of the reflected light is small and the resonant peak is sharp can be acquired, whereby the sensitivity of the sensor can be improved. Therefore, a sensor chip 1 capable of specifying a target substance from the SERS spectrum by improving the sensitivity of the sensor can be provided. By appropriately changing the period P1 and the height T1 of the first protrusion 11 and the height T2 of the second protrusion 12, the position of the resonant peak can be adjusted to an arbitrary wavelength. Accordingly, it is possible to appropriately select the light wavelength that is emitted when specifying a target substance, whereby the width of the measurement range increases.

In addition, according to this configuration, since the second protrusions 12 are disposed to have periodicity in the third direction parallel to the planar portion of the substrate 10, the period P2 of the second protrusion 12 can be appropriately changed. Accordingly, it is possible to appropriately select the light wavelength that is emitted when specifying a target substance, whereby the width of the measurement range increases.

In addition, according to this configuration, gold or silver is used as the metal of the surface of the diffraction grating 9, and accordingly, the LSPR and the SERS can be easily exhibited. Therefore, a target substance can be detected with high sensitivity.

In addition, according to this configuration, the duty ratio of the first protrusion 11 satisfies the relationship of "W1>W2", and accordingly, the spatial filling rate of the first protrusion 11 in which the LSPR is excited increases. Therefore, sensing can be performed under the condition of plasmon resonance that is broader than that of a case where the relationship of "W1<W2" is satisfied. In addition, the energy of light emitted when specifying a target substance can be effectively used.

In addition, also in a case where the duty ratio of the first protrusion 11 satisfies the relationship of "W1:W2=9:1", sensing can be performed under a wide plasmon resonance condition, and the energy of the emitted light can be effectively used.

In this embodiment, a structure in which the first protrusions 11 are arranged in the period P1 shorter than the light wavelength in the direction (the first direction) parallel to the planar portion of the substrate 10 is represented. However, the invention is not limited thereto. A sensor chip 4 that has a structure of the first protrusion that is different from that of the first protrusion 11 according to this embodiment will be described with reference to FIG. 15.

Figure 15:
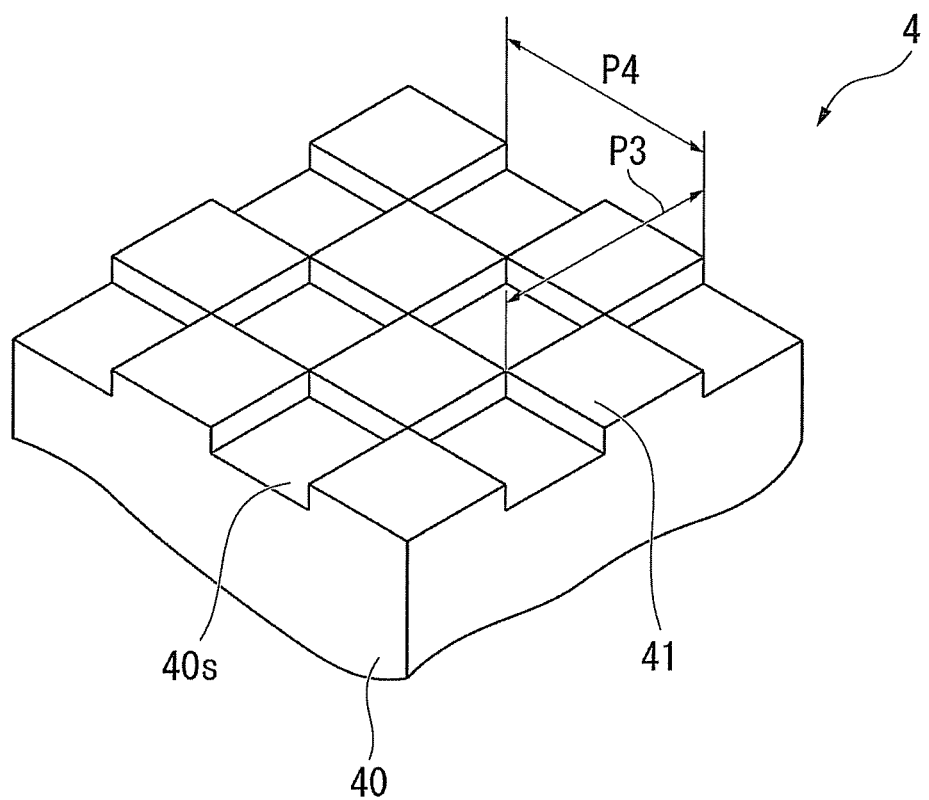
FIG. 15 is a schematic configuration diagram showing a modified example of a sensor chip having the first protrusions according to an embodiment of the invention.

FIG. 15 is a schematic perspective view showing the configuration of a sensor chip 4 that has the first protrusions 41 in a form different from that of the above-described first protrusions 11. In this figure, for convenience of the description, the second protrusion is not shown.

As shown in FIG. 15, the first protrusion 41 is formed on the planar portion 40s of a substrate 40. The first protrusions 41 are arranged in a period P3 shorter than the light wavelength in a direction (the first direction) parallel to the planar portion of the substrate 40. In addition, the first protrusions 41 are arranged in a period P4 that is shorter than the light wavelength in a second direction that is perpendicular to the first direction and is parallel to the planar portion of the substrate 40. Here, the second direction is not limited to the direction that is perpendicular to the first direction and is parallel to the planar portion of the substrate 40 and may be a direction that intersects the first direction and is parallel to the planar portion of the substrate 40.

According to this structure, sensing can be performed under a condition of plasmon resonance that is broader than that of a case where the first protrusions are formed only in the direction (the first direction) parallel to the planar portion of the substrate 10. Accordingly, a sensor chip 4 capable of specifying a target substance from the SERS spectrum by improving the sensitivity of the sensor can be provided. Furthermore, in addition to the period P3 of the first protrusions in the first direction, the period P4 in the second direction can be appropriately changed. Accordingly, the light wavelength emitted when specifying a target substance can be appropriately selected, whereby the width of the measurement range increases.

In this embodiment, a structure in which the second protrusions 12 are arranged in the period P2 shorter than the light wavelength in the direction (the third direction) parallel to the planar portion of the substrate 10, and more specifically, a structure in which the arrangement direction (the first direction) of the first protrusions 11 and the arrangement direction (the third direction) of the second protrusions 12 are the same direction is represented. However, the invention is not limited thereto. Thus, sensor chips 5, 6, 7, and 8 having a structure of the second protrusions that is different from that of the second protrusion 12 according to this embodiment will be described with reference to FIGS. 16A to 17B.

Figure 16A:
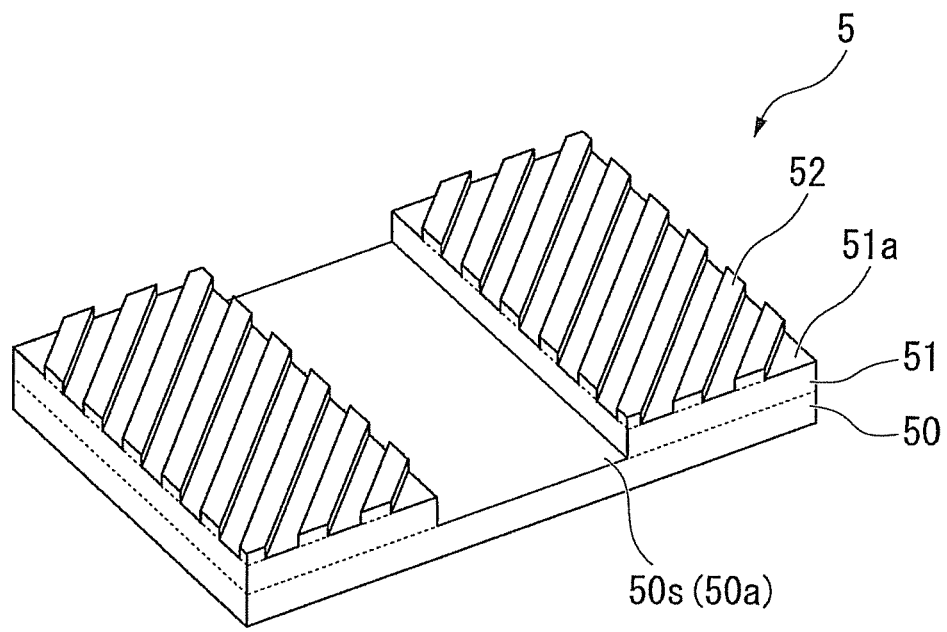
FIGS. 16A and 16B are schematic configuration diagrams showing modified examples of a sensor chip having the second protrusions.
Figure 16B:
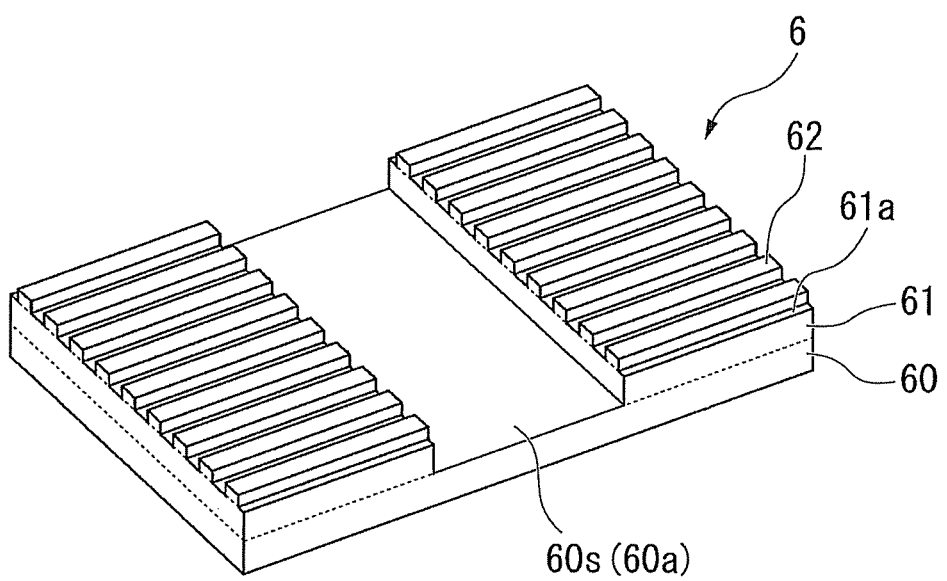

FIGS. 16A and 16B are schematic perspective views showing the configurations of sensor chips with the second protrusion different in form from the above-described second protrusion 12. FIG. 16A is a sensor chip 5 that has the second protrusion 52. FIG. 16B is a sensor chip 6 that has the second protrusion 62.

As shown in FIG. 16A, two or more of the second protrusions 52 are formed on only the upper face 51a of each of a plurality of the first protrusions 51 formed on the planar portion 50s of the substrate 50. In other words, the second protrusion 52 is not formed on the base portion 50a of the substrate 50. In the figure, as an example, a structure in which the intersection angle of the arrangement direction (the first direction) of the first protrusions 51 and the arrangement direction (the third direction) of the second protrusions 52 is 45 degrees is represented.

As shown in FIG. 16B, two or more of the second protrusions 62 are formed on only the upper face 61a of each of a plurality of the first protrusions 61 formed on the planar portion 60s of the substrate 60. In other words, the second protrusion 62 is not formed on the base portion 60a of the substrate 60. In the figure, as an example, a structure in which the intersection angle of the arrangement direction (the first direction) of the first protrusions 61 and the arrangement direction (the third direction) of the second protrusions 62 is 90 degrees is represented.

According to this configuration, a sensor chip capable of specifying a target substance from the SERS spectrum under a broad condition of plasmon resonance by improving the sensitivity of the sensor can be provided.

Figure 17A:
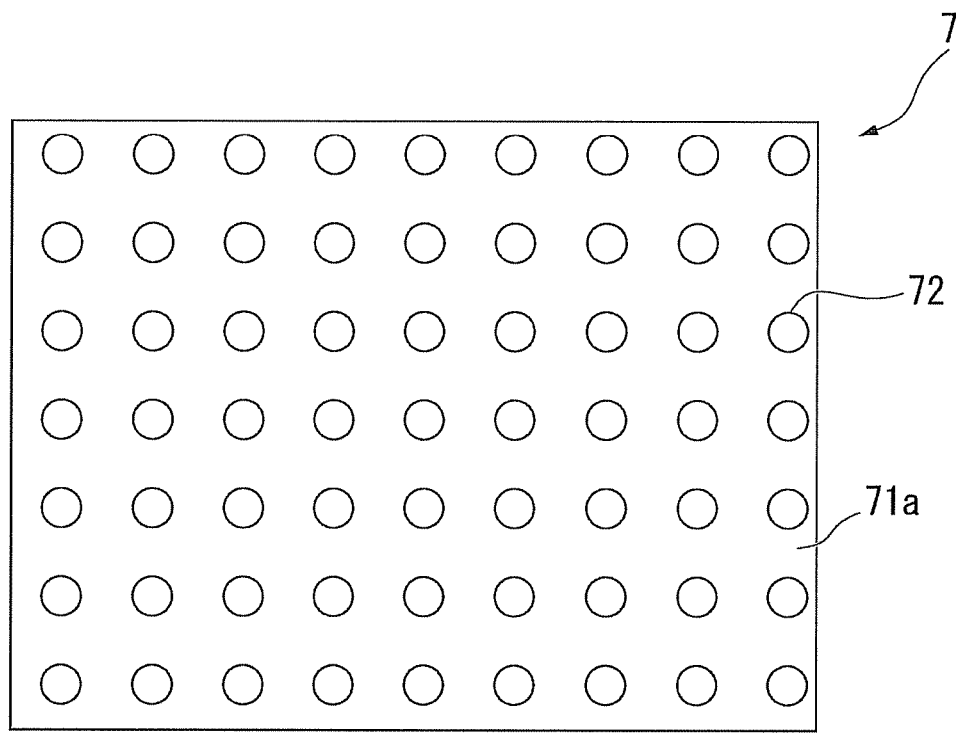
FIGS. 17A and 17B are schematic configuration diagrams showing modified examples of a sensor chip having the second protrusions.
Figure 17B:
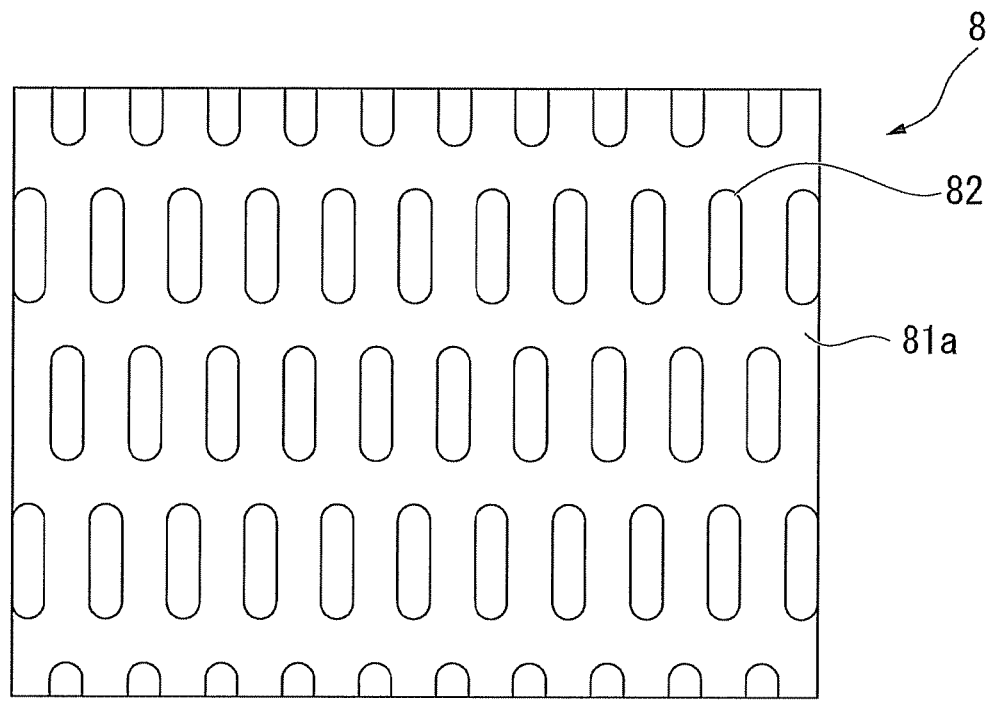

FIGS. 17A and 17B are enlarged plan views of sensor chips with the second protrusions that are different in form from the above-described second protrusions 12. FIG. 17A represents a sensor chip 7 with the second protrusions 72. FIG. 17B represents a sensor chip 8 with the second protrusions 82.

As shown in FIG. 17A, two or more of the second protrusions 72 are formed on only the upper face 71a of each of a plurality of the first protrusions (not shown). In addition, the second protrusions 72 are arranged so as to have periodicity in the fourth direction that intersects the third direction and is parallel to the planar portion of the substrate. In this figure, as an example, a structure in which the second protrusion 72 has a circle shape in the plan view is represented. Alternatively, the second protrusions 72 may be randomly disposed without having any periodicity.

As shown in FIG. 17B, two or more of the second protrusions 82 are formed on only the upper face 81a of each of a plurality of the first protrusions (not shown). In addition, the second protrusions 82 are arranged so as to have periodicity in the fourth direction that intersects the third direction and is parallel to the planar portion of the substrate. In this figure, as an example, a structure in which the second protrusion 82 has an oval shape in the plan view is represented. Alternatively, the second protrusions 82 may be randomly disposed without having any periodicity.

According to this configuration, sensing can be performed under a condition of plasmon resonance broader than that of a case where the second protrusions are formed only in the direction (the third direction) parallel to the planar portion of the substrate. Accordingly, a sensor chip capable of specifying a target substance from the SERS spectrum by improving the sensitivity of the sensor can be provided. Furthermore, in addition to the period of the second protrusions in the third direction, the period in the fourth direction can be appropriately changed. Accordingly, the light wavelength emitted when specifying a target substance can be appropriately selected, whereby the width of the measurement range increases.

In addition, in this embodiment, the second protrusions are formed by patterning the Au film formed on the upper face of the glass substrate. However, the invention is not limited thereto. For example, the second protrusions may be fine particles. According to such a configuration, a sensor chip capable of specifying a target substance from the SERS spectrum by improving the sensitivity of the sensor can be provided.

In addition, in this embodiment, as a metal contained in the substrate, a metal contained in the first protrusion, and a metal contained in the second protrusion, the same metal (gold or silver) is employed. However, the invention is not limited thereto. For example, different metals (gold, silver, copper, aluminum, or an alloy thereof) may be combined so as to be used, as in a case where the metal contained in the substrate is gold, the metal contained in the first protrusion is silver, and the metal contained in the second protrusion is an alloy of gold and silver or the like.

Analysis Apparatus

Figure 18:
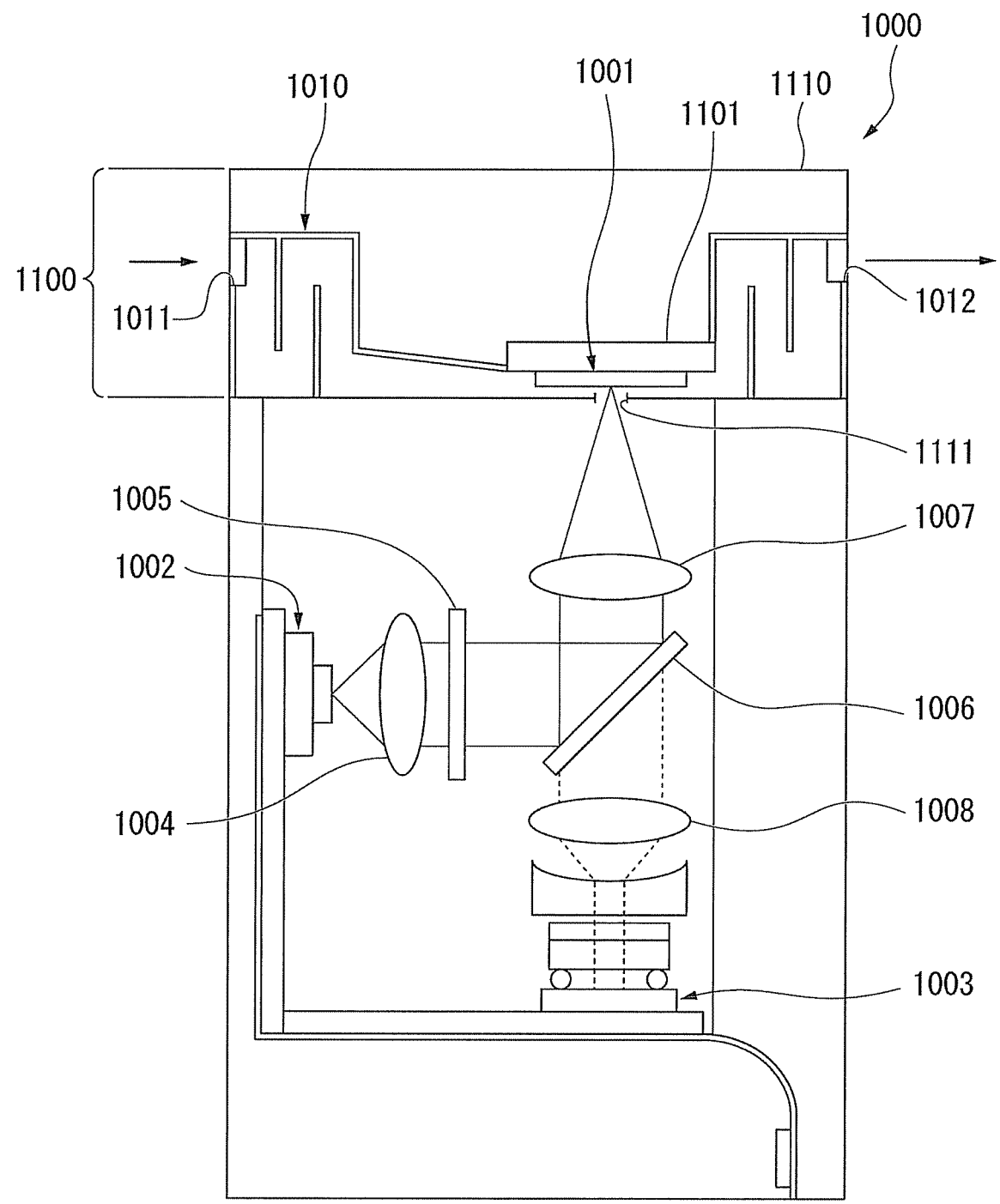
FIG. 18 is a schematic diagram representing an example of an analysis apparatus.

FIG. 18 is a schematic diagram representing an example of an analysis apparatus that includes a sensor chip according to an embodiment of the invention. In addition, arrows shown in FIG. 18 represent the transport direction of a target substance (not shown).

As shown in FIG. 18, the analysis apparatus 1000 includes a sensor chip 1001, a light source 1002, a photo detector 1003, a collimator lens 1004, a polarization control device 1005, a dichroic mirror 1006, an objective lens 1007, an objective lens 1008, and a transport unit 1010. The light source 1002 and the photo detector 1003 are electrically connected to a control device (not shown) through wirings.

The light source 1002 generates a laser beam that excites the SPP, the LSPR, and the SERS. The laser beam emitted from the light source 1002 becomes a parallel beam through the collimator lens 1004, passes through the polarization control device 1005, is guided in the direction of the sensor chip 1001 by the dichroic mirror 1006 so as to be collected to the objective lens 1007, and is incident to the sensor chip 1001. At this time, on the surface (for example, a face on which a metal nanostructure or a detection substance selecting mechanism is formed) of the sensor chip 1001, a target substance (not shown) is placed. In addition, by controlling the driving of a fan (not shown), the target substance is introduced into the inside of the transport unit 1010 from a loading entrance 1011 and is discharged from a discharge opening 1012 to the outside of the transport unit 1010. The size of the metal nanostructure is smaller than the wavelength of the laser beam.

When the laser beam is incident to the metal nanostructure, free electrons are in a state of resonant oscillation accompanying the oscillation of the laser beam, and a strong surface localized electric field is excited near the metal nanostructure, whereby the LSPR is excited. Then, when the distance between the metal nanostructures adjacent to each other is shortened, an extremely strong electric field is generated near the contact point. When one to several target substances are adsorbed on the contact point, the SERS is generated from the contact point.

The light (Raman scattering light or Rayleigh scattering light) acquired by the sensor chip 1001 passes through the objective lens 1007, is guided in the direction of the photo detector 1003 by the dichroic mirror 1006 so as to be collected to the objective lens 1007, and is incident to the photo detector 1003. Then, the light is resolved in a spectrum by the photo detector 1003, whereby spectrum information can be acquired.

According to this configuration, since the above-described sensor chip according to an embodiment of the invention is included, the target molecule can be detected by performing selective spectroscopy for the Raman scattering light. Therefore, an analysis apparatus 1000 capable of specifying a target substance from the SERS spectrum by improving the sensitivity of the sensor can be provided.

The analysis apparatus 1000 includes a sensor cartridge 1100. The sensor cartridge 1100 includes the sensor chip 1001, the transport unit 1010 that transports a target substance to the surface of the sensor chip 1001, a placement unit 1101 in which the sensor chip 1001 is placed, and a casing 1110 that houses the above-described units. In a position of the casing 1110 that faces the sensor chip 1001, an irradiation window 1111 is disposed. The laser beam emitted from the light source 1002 passes through the irradiation window 1111 and is emitted to the surface of the sensor chip 1001. The sensor cartridge 1100 is located in the upper portion of the analysis apparatus 1000 and is detachably attached to the main unit of the analysis apparatus 1000.

According to this configuration, since the above-described sensor chip according to an embodiment of the invention is included, the target molecule can be detected by performing selective spectroscopy for the Raman scattering light. Therefore, a sensor cartridge 1100 capable of specifying a target substance from the SERS spectrum by improving the sensitivity of the sensor can be provided.

The analysis apparatus according to an embodiment of the invention can be broadly applied to medical treatments or physical examinations, detection of drugs or explosive substances, and a sensing apparatus used for inspection of foodstuffs. In addition, the analysis apparatus can be used as an affinity sensor or the like that detects whether or not a substance is adsorbed, including whether or not an antigen is adsorbed in an antigen-antibody reaction.

What is claimed is:

1. A sensor chip comprising:
a substrate that has a planar portion; and
a diffraction grating on the planar portion and having a metal surface, the diffraction grating having a target substance thereon and including:
a plurality of first protrusions periodically arranged in a period equal to or greater than 100 nm and equal to or less than 1000 nm in a first direction parallel to the planar portion;
a plurality of base portions that are located between two adjacent first protrusions and that configure a base of the substrate; and
a plurality of second protrusions that are periodically arranged on upper faces of the plurality of first protrusions.

2. The sensor chip according to claim 1, wherein the plurality of first protrusions is periodically arranged in a second direction that intersects the first direction and is parallel to the planar portion.

3. The sensor chip according to claim 1, wherein the plurality of second protrusions is periodically arranged in a third direction that is parallel to the planar portion.

4. The sensor chip according to claim 3, wherein the plurality of second protrusions is periodically arranged in a fourth direction that intersects the third direction and is parallel to the planar portion.

5. The sensor chip according to claim 1, wherein the plurality of second protrusions comprises fine particles.

6. The sensor chip according to claim 1, wherein, when a width of the first protrusion in the first direction is denoted by W1, and a distance between two adjacent first protrusions in the first direction is denoted by W2, relationship of "W1>W2" is satisfied.

7. The sensor chip according to claim 6, wherein a ratio of the width W1 of the first protrusion in the first direction to the distance W2 between the two adjacent first protrusions in the first direction satisfies relationship of "W1:W2=9:1".

8. The sensor chip according to claim 1, wherein the metal surface of the diffraction grating is one of gold and silver.

9. A sensor cartridge comprising:
the sensor chip according to claim 1;
a transport unit that transports the target substance to a surface of the sensor chip;
a placement unit in which the sensor chip is placed;
a casing that houses the sensor chip, the transport unit, and the placement unit; and
an irradiation window that is disposed at a position facing the surface of the sensor chip on the casing.

10. An analysis apparatus comprising:
the sensor chip according to claim 1;
a light source that emits light to the sensor chip; and
a photo detector that detects light scattered by the sensor chip.

11. A sensor chip comprising:
a substrate that has a planar portion; and
a diffraction grating having a composite pattern in the planar portion and a metal surface, the diffraction grating having a target substance thereon and superimposedly including:
a first protrusion pattern in which a plurality of first protrusions is periodically arranged in a period equal to or greater than 100 nm and equal to or less than 1000 nm; and
a second protrusion pattern in which a plurality of second protrusions is periodically arranged in the plurality of first protrusions in a period shorter than that of the first protrusion pattern.

12. The sensor chip according to claim 11, wherein the plurality of first protrusions is periodically arranged in a first direction that is parallel to the planar portion and is periodically arranged in a second direction that intersects the first direction and is parallel to the planar portion.

13. The sensor chip according to claim 11, wherein the plurality of second protrusions is periodically arranged in a third direction that is parallel to the planar portion.

14. The sensor chip according to claim 13, wherein the plurality of second protrusions is periodically arranged in a fourth direction that intersects the third direction and is parallel to the planar portion.

15. The sensor chip according to claim 11, wherein the plurality of second protrusions comprises fine particles.

16. The sensor chip according to claim 11, wherein, when a width of the first protrusion in the first direction is denoted by W1, and a distance between two adjacent first protrusions in the first direction is denoted by W2, relationship of "W1>W2" is satisfied.

17. The sensor chip according to claim 16, wherein a ratio of the width W1 of the first protrusion in the first direction to the distance W2 between the two adjacent first protrusions in the first direction satisfies relationship of "W1:W2=9:1".

18. The sensor chip according to claim 11, wherein the metal surface of the diffraction grating is one of gold and silver.

19. A sensor cartridge comprising:
   the sensor chip according to claim 11;
   a transport unit that transports the target substance to a surface of the sensor chip;
   a placement unit in which the sensor chip is placed;
   a casing that houses the sensor chip, the transport unit, and the placement unit; and
   an irradiation window that is disposed at a position facing the surface of the sensor chip on the casing.

20. An analysis apparatus comprising:
   the sensor chip according to claim 11;
   a light source that emits light onto the sensor chip; and
   a photo detector that detects light scattered by the sensor chip.

* * * * *